United States Patent
Nakayama

(10) Patent No.: US 11,103,206 B2
(45) Date of Patent: Aug. 31, 2021

(54) MAMMOGRAPHY APPARATUS, RADIATION IMAGE CAPTURING SYSTEM, IMAGE PROCESSING APPARATUS, CONTROL METHOD, IMAGE PROCESSING METHOD, CONTROL PROGRAM, AND IMAGE PROCESSING PROGRAM

(71) Applicant: FUJIFILM CORPORATION, Tokyo (JP)

(72) Inventor: Hiroki Nakayama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 73 days.

(21) Appl. No.: 16/742,938

(22) Filed: Jan. 15, 2020

(65) Prior Publication Data

US 2020/0146645 A1     May 14, 2020

Related U.S. Application Data

(63) Continuation of application No. PCT/JP2018/027149, filed on Jul. 19, 2018.

(30) Foreign Application Priority Data

Jul. 19, 2017   (JP) .............................. JP2017-140326

(51) Int. Cl.
    *A61B 6/00*         (2006.01)
    *A61B 6/03*         (2006.01)

(52) U.S. Cl.
    CPC .............. *A61B 6/502* (2013.01); *A61B 6/032* (2013.01); *A61B 6/4476* (2013.01); *A61B 6/463* (2013.01); *A61B 6/5235* (2013.01); *A61B 6/542* (2013.01)

(58) Field of Classification Search
CPC ....... A61B 6/502; A61B 6/032; A61B 6/4476; A61B 6/463; A61B 6/4312; A61B 6/5235; A61B 6/542; A61B 6/025; A61B 6/482

See application file for complete search history.

(56) References Cited

U.S. PATENT DOCUMENTS

2014/0376691 A1* 12/2014 Hoernig ................. A61B 6/502
                                                                    378/37
2016/0235380 A1    8/2016   Smith et al.

FOREIGN PATENT DOCUMENTS

DE       102011088749 A1     6/2013
GB            2533632 A     6/2016

(Continued)

OTHER PUBLICATIONS

English language translation of the following: Office action dated Oct. 6, 2020 from the JPO in a Japanese patent application No. 2019-530597 corresponding to the instant patent application.

(Continued)

*Primary Examiner* — Courtney D Thomas
(74) *Attorney, Agent, or Firm* — Solaris Intellectual Property Group, PLLC

(57) ABSTRACT

A mammography apparatus includes a radiation source driver that moves a radiation source to a plurality of imaging positions including a first imaging position where LE imaging of emitting radiation R with low energy from the radiation source to capture a radiation image is performed, and a second imaging position where the LE imaging and HE imaging of emitting radiation R with high energy to capture a radiation image are performed, and a controller that causes a radiation detector to perform the LE imaging at the first imaging position in a state where the radiation source is moved, and causes the radiation detector to perform the LE imaging and the HE imaging at the second (Continued)

imaging position in a state where the movement of the radiation source is stopped or the radiation source is moved at a moving speed slower than that at the first imaging position.

18 Claims, 18 Drawing Sheets

(56) References Cited

FOREIGN PATENT DOCUMENTS

| | | | |
|---|---|---|---|
| JP | 2012-24424 | A | 2/2012 |
| JP | 2012-166026 | A | 9/2012 |
| JP | 2014-518111 | A | 7/2014 |
| JP | 2016-135319 | A | 7/2016 |
| JP | 2016-533803 | A | 11/2016 |
| JP | 2017-60559 | A | 3/2017 |
| WO | 2010028208 | A1 | 3/2010 |
| WO | 2013004573 | A1 | 1/2013 |

OTHER PUBLICATIONS

International Search Report issued in International Application No. PCT/JP2018/027149 dated Oct. 23, 2018.
Written Opinion of the ISA issued in International Application No. PCT/JP2018/027149 dated Oct. 23, 2018.
Office Action dated Jun. 4, 2020, issued by the EPO in corresponding EP Patent Application No. EP18836012.7.

* cited by examiner

MAMMOGRAPHY APPARATUS, RADIATION IMAGE CAPTURING SYSTEM, IMAGE PROCESSING APPARATUS, CONTROL METHOD, IMAGE PROCESSING METHOD, CONTROL PROGRAM, AND IMAGE PROCESSING PROGRAM

CROSS-REFERENCE TO RELATED APPLICATION

This application is a continuation application of International Application No. PCT/JP2018/027149, filed Jul. 19, 2018, the disclosure of which is incorporated herein by reference in its entirety. Further, this application claims priority from Japanese Patent Application No. 2017-140326, filed Jul. 19, 2017, the disclosure of which is incorporated herein by reference in its entirety.

BACKGROUND OF THE INVENTION

1. Field of the Invention

The present invention relates to a mammography apparatus, a radiation image capturing system, an image processing apparatus, a control method, an image processing method, a control program, and an image processing program.

2. Description of the Related Art

A mammography apparatus that emits radiation toward a mamma of a test subject from a radiation source and detects the radiation having passed through the mamma using a radiation detector to capture a radiation image is known.

As imaging using the mammography apparatus, so-called tomosynthesis imaging in which radiation is emitted toward a mamma while varying an incidence angle of the radiation in a predetermined range and imaging is performed at each of a plurality of different incidence angles is known.

In addition, in general, so-called dual-energy subtraction imaging of obtaining a differential image between a first radiation image captured by a radiation detector by emitting radiation with first energy and a second radiation image captured by the radiation detector by emitting radiation with second energy different from the first energy is known. Further, imaging obtained by combining the tomosynthesis imaging and the dual-energy subtraction imaging, in which the first radiation image and the second radiation image are captured at each of a plurality of different incidence angles and differential images are obtained is also performed.

For example, JP2012-166026A discloses a mammography apparatus capable of performing normal tomosynthesis imaging and imaging obtained by combining the tomosynthesis imaging and the dual-energy subtraction imaging.

SUMMARY OF THE INVENTION

Regarding imaging for the same subject (mamma), in a case where normal tomosynthesis imaging and imaging obtained by combining the tomosynthesis imaging and the dual-energy subtraction imaging are performed as disclosed in JP2012-166026A, the time required until the capturing of all the radiation images is completed is increased. In general, in the mammography apparatus, imaging is performed in a state where the mamma is pressed by the pressing plate. In a case where the time required until the capturing of the radiation image is completed is increased, the time for which the mamma is pressed by the pressing plate is also increased, which becomes a burden on the test subject. Therefore, a technique of further reducing the time required until imaging is completed is desired.

The present disclosure is made in view of the above-described circumstances, and an object of the present disclosure is to provide a mammography apparatus, a radiation image capturing system, an image processing apparatus, a control method, an image processing method, a control program, and an image processing program which can further reduce the time required until the capturing of a radiation image is completed.

A mammography apparatus according to a first aspect of the present disclosure comprises a radiation source driver that moves a radiation source to a plurality of imaging positions including a first imaging position where first imaging of emitting radiation with first energy from the radiation source to capture a radiation image by a radiation detector is performed, and a second imaging position where the first imaging and second imaging of emitting radiation with second energy different from the first energy from the radiation source to capture a radiation image by the radiation detector are performed, and a controller that causes the radiation detector to perform the first imaging at the first imaging position in a state where the radiation source is moved by the radiation source driver, and causes the radiation detector to perform the first imaging and the second imaging at the second imaging position in a state where the movement of the radiation source is stopped or the radiation source is moved at a moving speed slower than that at the first imaging position by the radiation source driver.

In the mammography apparatus according to a second aspect of the present disclosure, in the mammography apparatus according to the first aspect, the controller performs control such that an irradiation time for which radiation is emitted from the radiation source in the first imaging is shorter than an irradiation time for which radiation is emitted from the radiation source in the second imaging.

In the mammography apparatus according to a third aspect of the present disclosure, in the mammography apparatus according to the first or second aspect, the first energy is lower than the second energy.

In the mammography apparatus according to a fourth aspect of the present disclosure, in the mammography apparatus according to the first or second aspect, the first energy is higher than the second energy.

In the mammography apparatus according to a fifth aspect of the present disclosure, in the mammography apparatus according to the first or second aspect, the controller performs control such that a dose of the radiation emitted from the radiation source in the first imaging is smaller than a dose of the radiation emitted from the radiation source in the second imaging in a case where the first energy is lower than the second energy.

In the mammography apparatus according to a sixth aspect of the present disclosure, in the mammography apparatus according to the first or second aspect, the controller performs control such that a dose of the radiation emitted from the radiation source in the first imaging at the second imaging position is smaller than a dose of the radiation emitted from the radiation source in the first imaging at the first imaging position in a case where the first energy is lower than the second energy.

In the mammography apparatus according to a seventh aspect of the present disclosure, in the mammography apparatus according to any one of the first to fourth aspects, the controller performs control such that a dose of the radiation emitted from the radiation source in the first imaging at the second imaging position and a dose of the radiation emitted from the radiation source in the second imaging at the second imaging position are smaller than a dose of the radiation emitted from the radiation source in the first imaging at the first imaging position.

In the mammography apparatus according to an eighth aspect of the present disclosure, in the mammography apparatus according to any one of the first to seventh aspects, the first energy and the second energy are determined depending on a k absorption end of a contrast medium used in contrast imaging.

In addition, a radiation image capturing system according to a ninth aspect of the present disclosure comprises the mammography apparatus according to any one of the first to eighth aspects; and an image generation unit that acquires a plurality of first radiation images captured in first imaging and a plurality of second radiation images captured in second imaging from the mammography apparatus, generates a tomographic image reconstructed using the plurality of first radiation images, generates a differential image between the plurality of first radiation images at the second imaging position and the plurality of second radiation images at the second imaging position for each second imaging position, and generates a differential tomographic image reconstructed using each generated differential image.

The radiation image capturing system according to a tenth aspect of the present disclosure, in the radiation image capturing system according to the ninth aspect, further comprises a deriving unit that derives a position of an interesting object of a subject, from the differential tomographic image.

In the radiation image capturing system according to an eleventh aspect of the present disclosure, in the radiation image capturing system according to the ninth or tenth aspect, the image generation unit derives a region of the tomographic image corresponding to a region of an interesting object of a subject detected in the differential tomographic image, and displays the tomographic image in which the derived region is emphasized on a display.

In the radiation image capturing system according to a twelfth aspect of the present disclosure, in the radiation image capturing system according to any one of the ninth to eleventh aspects, the image generation unit displays the tomographic image and the differential tomographic image side by side on a display.

In the radiation image capturing system according to a thirteenth aspect of the present disclosure, in the radiation image capturing system according to any one of the ninth to eleventh aspects, the image generation unit displays the tomographic image and the differential tomographic image in a superimposed manner on a display.

In addition, an image processing apparatus according to a fourteenth aspect of the present disclosure comprises an acquisition unit that acquires a plurality of first radiation images captured in first imaging and a plurality of second radiation images captured in second imaging from the mammography apparatus according to the aspects of the present disclosure; and an image generation unit that generates a tomographic image reconstructed using the plurality of first radiation images acquired by the acquisition unit, generates a differential image between the plurality of first radiation images captured in the first imaging at the second imaging position and the plurality of second radiation images for each second imaging position, and generates a differential tomographic image reconstructed using the generated differential image.

In addition, a control method of a mammography apparatus comprising a radiation source driver that moves a radiation source to a plurality of imaging positions including a first imaging position where first imaging of emitting radiation with first energy from the radiation source to capture a radiation image by a radiation detector is performed, and a second imaging position where the first imaging and second imaging of emitting radiation with second energy different from the first energy from the radiation source to capture a radiation image by the radiation detector are performed, the control method according to a fifteenth aspect of the present disclosure comprises the processes of controlling for causing the radiation detector to perform the first imaging at the first imaging position in a state where the radiation source is moved by the radiation source driver, and controlling for causing the radiation detector to perform the first imaging and the second imaging at the second imaging position in a state where the movement of the radiation source is stopped or the radiation source is moved at a moving speed slower than a moving speed at the first imaging position by the radiation source driver.

In addition, an image processing method according to a sixteenth aspect of the present disclosure comprises the processes of acquiring a plurality of first radiation images captured in first imaging and a plurality of second radiation images captured in second imaging from the mammography apparatus according to the aspects of the present disclosure, generating a tomographic image reconstructed using the plurality of acquired first radiation images, generating a differential image between the plurality of first radiation images captured in the first imaging at the second imaging position and the plurality of second radiation images for each second imaging position, and generating a differential tomographic image reconstructed using the generated differential image.

In addition, a control program of a mammography apparatus comprising a radiation source driver that moves a radiation source to a plurality of imaging positions including a first imaging position where first imaging of emitting radiation with first energy from the radiation source to capture a radiation image by a radiation detector is performed, and a second imaging position where the first imaging and second imaging of emitting radiation with second energy different from the first energy from the radiation source to capture a radiation image by the radiation detector are performed, the control program according to a seventeenth aspect of the present disclosure cases a computer to execute the processes of controlling for causing the radiation detector to perform the first imaging at the first imaging position in a state where the radiation source is moved by the radiation source driver, and controlling for causing the radiation detector to perform the first imaging and the second imaging at the second imaging position in a state where the movement of the radiation source is stopped or the radiation source is moved at a moving speed slower than a moving speed at the first imaging position by the radiation source driver.

In addition, an image processing program according to an eighteenth aspect of the present disclosure causes a computer to execute a process of acquiring a plurality of first radiation images captured in first imaging and a plurality of second radiation images captured in second imaging from the mammography apparatus according to the aspects of the present disclosure, generating a tomographic image reconstructed using the plurality of acquired first radiation images, generating a differential image between the plurality of first radiation images captured in the first imaging at the second imaging position and the plurality of second radiation images for each second imaging position, and generating a differential tomographic image reconstructed using the generated differential image.

A control device according to an aspect of the present disclosure is a control device including a processor, of a mammography apparatus comprising a radiation source driver that moves a radiation source to a plurality of imaging positions including a first imaging position where first imaging of emitting radiation with first energy from the radiation source to capture a radiation image by a radiation detector is performed, and a second imaging position where the first imaging and second imaging of emitting radiation with second energy different from the first energy from the radiation source to capture a radiation image by the radiation detector are performed. The processor performs control such that the first imaging is performed by the radiation detector at the first imaging position in a state where the radiation source is moved by the radiation source driver, and control such that the first imaging and the second imaging are performed by the radiation detector at the second imaging position in a state where the movement of the radiation source is stopped or the radiation source is moved at a moving speed slower than a moving speed at the first imaging position by the radiation source driver.

An image processing apparatus according to an aspect of the present disclosure is an image processing apparatus including a processor, and the processor acquires a plurality of first radiation images captured in first imaging and a plurality of second radiation images captured in second imaging from the mammography apparatus according to the aspects of the present disclosure, generates a tomographic image reconstructed using the plurality of acquired first radiation images, generates a differential image between the plurality of first radiation images captured in the first imaging at the second imaging position and the plurality of second radiation images for each second imaging position, and generates a differential tomographic image reconstructed using the generated differential image.

According to the present disclosure, it is possible to further reduce the time required until capturing of the radiation image is completed.

DESCRIPTION OF THE PREFERRED EMBODIMENTS

Figure 1:
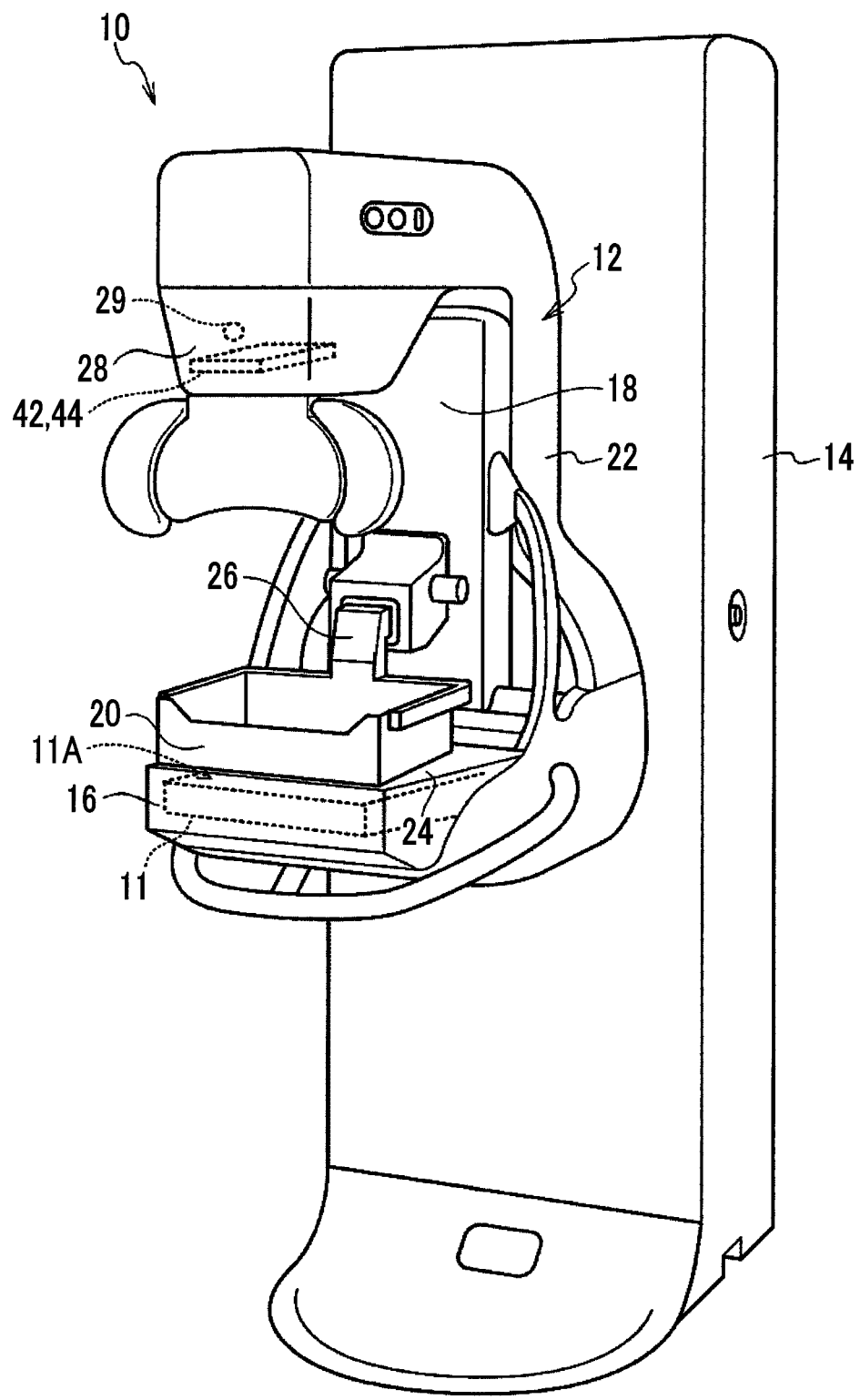
FIG. 1 is a diagram showing an example of an entire configuration of a mammography apparatus according to a first embodiment, which is a perspective view when seen from a breast wall side of a test subject.

Hereinafter, embodiments of the invention will be described in detail with reference to the accompanying drawings. The embodiments do not limit the invention.

First Embodiment

First, an example of the entire configuration of a mammography apparatus of the embodiment will be described with reference to FIG. 1.

A mammography apparatus 10 of the embodiment is an apparatus that individually emits radiation (for example, X-rays) to right and left mammae of a test subject to individually capture radiation images of the right and left mammae. The mammography apparatus 10 may be an apparatus that images a mamma of a test subject in a state where the test subject is standing (standing position state), or in a state where the test subject sits on a chair (including a wheelchair) (sitting position state). That is, the mammography apparatus 10 may be an apparatus capable of capturing at least radiation images of the right and left mammae of the test subject.

Further, the mammography apparatus 10 of the embodiment has a function of performing so-called tomosynthesis imaging (of which details will be described below) and simple imaging. In the embodiment, imaging other than the tomosynthesis imaging is referred to as "simple imaging".

The mammography apparatus 10 of the embodiment has a function of performing so-called dual-energy subtraction imaging (hereinafter, referred to as "dual imaging") in the tomosynthesis imaging. Further, the mammography apparatus 10 of the embodiment has a contrast enhanced spectral mammography (CESM) function of performing dual imaging in case of performing so-called contrast imaging in which imaging is performed in a state where a contrast medium is administered to the mamma of a test subject, which will be described in detail below. In the embodiment, tomosynthesis imaging in case of not performing dual imaging is referred to as "normal tomosynthesis imaging".

The mammography apparatus 10 of the embodiment has a function of performing imaging by combining both the normal tomosynthesis imaging and the dual imaging. Hereinafter, imaging in which both the normal tomosynthesis imaging and the dual imaging are combined to be performed is referred to as "combination imaging".

In this manner, the mammography apparatus 10 of the embodiment has a function of performing imaging corresponding to four imaging modes of simple imaging, normal tomosynthesis imaging, dual imaging, and combination imaging, as imaging modes (types of imaging).

In addition, in the following description, it is assumed that, in capturing a radiation image, a side (breast wall side) close to a test subject in a case where the test subject faces the mammography apparatus 10 is an apparatus front side of the mammography apparatus 10 and a side distant from the test subject in a case where the test subject faces the mammography apparatus 10 is an apparatus rear side of the mammography apparatus 10. Further, in the description, it is assumed that a lateral direction of the test subject in a case where the test subject faces the mammography apparatus 10 is an apparatus lateral direction of the mammography apparatus 10. In addition, in the description, it is assumed that a direction in which the side of the head of the test subject is an upper side and the side of the feet is a lower side in a case where the test subject faces the mammography apparatus 10 is a vertical direction.

As shown in FIG. 1, the mammography apparatus 10 includes an imaging part 12 that has an approximately C-shape in a side view and is provided on the apparatus front side, and a base stand part 14 that supports the imaging part 12 from the apparatus rear side.

The imaging part 12 includes an imaging stand 16 having a planar imaging surface 24 that comes into contact with the mamma of the test subject in a standing position state, a pressing plate 20 for pressing the mamma in a state where the mamma is interposed between the imaging surface 24 of the imaging stand 16 and the pressing plate 20, and a holding part 18 that supports the imaging stand 16 and the pressing plate 20. A member that transmits radiation is used for the pressing plate 20.

Further, the imaging part 12 includes a support part 22 that supports a radiation source 29, and a radiation irradiation part 28, and the support part 22 is separated from the holding part 18.

As shown in FIG. 1, the radiation source 29 including a bulb (in the embodiment, for example, tungsten) that emits radiation to the mamma is provided inside the radiation irradiation part 28 of the mammography apparatus 10 of the embodiment. Further, a rhodium (Rh) filter 42 and a copper (Cu) filter 44 are included inside the radiation irradiation part 28 so as be positioned between the radiation source 29 and the imaging stand 16. FIG. 1 shows the Rh filter 42 and the Cu filter 44 in an integrated manner, but each filter is provided as an individual filter.

In general, in imaging in the mammography apparatus 10, it is possible to clarify contrast of a captured radiation image, using radiation of an energy component of 15 keV to 20 keV. In radiation of energy lower than the above-described range (in a case where the energy component is smaller than 15 keV), since radiation exposure to a test subject (mamma) occurs, the radiation does not almost contribute to a radiation image. On the other hand, in radiation of energy higher than the above-described range (in a case where the energy component exceeds 20 keV), since a transmittance at which the radiation passes through the test subject (mamma) is high, contrast of a captured radiation image is lowered, which may lead to deterioration in image quality in some cases. Since the Rh filter 42 shows 23.2 keV at a k absorption end, it is possible to reduce radiation of an energy component of 23.2 keV or greater, and to reduce radiation of a low energy component as the thickness of the filter becomes large. Accordingly, in the mammography apparatus 10, by using the Rh filter 42, a spectrum of radiation to be emitted to a subject can be set in an energy region of a desired range (15 keV to 20 keV). In this way, in the mammography apparatus 10, by using the Rh filter 42, it is possible to reduce deterioration in image quality of a radiation image, and to reduce the amount of radiation exposure to a test subject.

Therefore, in the mammography apparatus 10 of the embodiment, in a case where simple imaging and normal tomosynthesis imaging are performed, imaging is performed using the Rh filter 42.

On the other hand, as a contrast medium used in contrast imaging, an iodine contrast medium of which a k absorption end is 32 keV is generally used. In this contrast imaging (dual imaging), two times of imaging, that is, imaging in which radiation of energy lower than the k absorption end of the iodine contrast medium is emitted and imaging in which radiation of energy higher than the k absorption end of the iodine contrast medium is emitted are performed. Then, a concentration distribution of the contrast medium is calculated from a difference of image data of the obtained two radiation images, and the contrast medium is imaged.

Since the Cu filter 44 shows 9.0 keV at a k absorption end, it is possible to reduce radiation of an energy component of 9.0 keV or smaller. Therefore, in the mammography apparatus 10 of the embodiment, in contrast imaging, in case of performing imaging in which radiation of energy higher than the k absorption end is emitted, imaging is performed using the Cu filter 44. Further, in the mammography apparatus 10, by using the Cu filter 44, it is possible to reduce radiation of 9.0 keV or smaller, and thus, it is possible to reduce the amount of radiation exposure to the test subject.

Further, in the mammography apparatus 10 of the embodiment, in contrast imaging, in case of performing imaging in which radiation of energy lower than the k absorption end is emitted, imaging is performed using the Rh filter 42.

Filters included in the mammography apparatus 10 are not limited to the Rh filter 42 and the Cu filter 44, and the filters used according to the imaging are not limited to the aspects of the embodiment. For example, since an Al filter has a low attenuation factor of radiation compared with the Rh filter 42, the Al filter is suitable for tomosynthesis imaging where imaging is performed in a short imaging time (irradiation time of radiation) at each imaging position in a state where the radiation source 29 is continuously moved. Therefore, for example, in a case where normal tomosynthesis imaging is performed, imaging may be performed using an Al filter.

Further, a moving part (not shown) is provided inside the radiation irradiation part 28, and in a case where capturing of a radiation image is performed, the moving part moves one of the Rh filter 42 and the Cu filter 44 according to the imaging mode to a position within an irradiation field.

In addition, a shaft (not shown) is provided in the imaging part 12 of the embodiment, so that the imaging part 12 is able to rotate with respect to the base stand part 14. The shaft is fixed with respect to the support part 22, and the shaft and the support part 22 integrally rotate.

Gears are respectively provided in the shaft provided in the imaging part 12 and the holding part 18, and an engagement state and a non-engagement state of the gears are switched, so that a state where the holding part 18 and the shaft are connected to each other to integrally rotate and a state where the shaft is spaced from the holding part 18 to idly rotate can be switched. The switching between transmission of power of the shaft and non-transmission thereof is not limited to the above-described gears, and instead, a variety of machine elements may be used.

The holding part 18 supports the imaging stand 16 and the radiation source 29 while causing the imaging surface 24 and the radiation source 29 to be spaced from each other by a predetermined interval. Further, the holding part 18 also holds the pressing plate 20 through a support arm 26, the holding part 18 slides the support arm 26 to move the pressing plate 20, and thus, an interval between the pressing plate 20 and the imaging surface 24 is changed.

The imaging surface 24 with which the mamma of the test subject come into contact is formed of carbon, from a viewpoint of radiability or strength, for example. Inside the imaging stand 16, a radiation detector 11 that detects radiation that passes through the mamma and the imaging surface 24 is disposed. A radiation image is generated on the basis of the radiation detected by the radiation detector 11. The type of the radiation detector 11 of the embodiment is not particularly limited, and the radiation detector may be, for example, a radiation detector of an indirect conversion type that converts radiation into light and converts the converted light into electric charges, or may be a radiation detector of a direct conversion type that directly converts radiation into electric charges. In the mammography apparatus 10 of the embodiment, image data indicating a radiation image output from the radiation detector 11 is transmitted to a console 6 (refer to FIG. 3).

Figure 2:
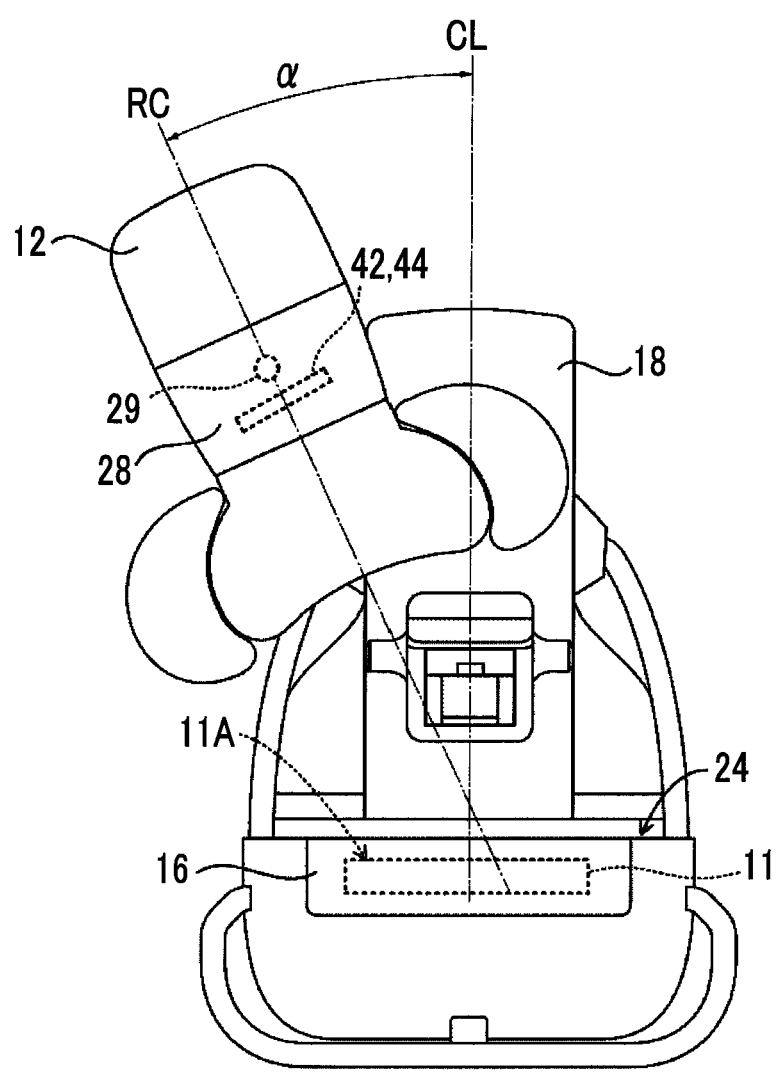
FIG. 2 is a diagram for describing tomosynthesis imaging in the mammography apparatus according to the first embodiment.

The mammography apparatus 10 of the embodiment may emit radiation from the radiation source 29 while varying an incidence angle of the radiation in a predetermined range, as shown in FIG. 2, and may perform imaging (so-called tomosynthesis imaging) at each of different incidence angles. Here, the "incidence angle" refers to an angle formed by a normal line CL of a detection surface 11A of the radiation detector 11 and a radiation axis RC, and corresponds to an irradiation angle at which radiation is emitted from the radiation source 29. Accordingly, in a case where the normal line CL and the radiation axis RC are the same, the incidence angle becomes 0 degrees. Here, it is assumed that the detection surface 11A of the radiation detector 11 is a surface that is approximately parallel to the imaging surface 24.

In the embodiment, as shown in FIG. 2, imaging is performed whenever the radiation source 29 is positioned at each of imaging positions of a plurality of places while moving the position of the radiation source 29 in order to change the incidence angle of the radiation from an angle α at an interval of a predetermined angle θ.

In the mammography apparatus 10 of the embodiment, in cases other than a case where the incidence angle of radiation is 0 degrees, imaging is performed at each imaging position while continuously moving the radiation source 29. As an imaging method in a case where the radiation source 29 is continuously moved, for example, a method for continuously moving the radiation source 29 without stopping the movement of the radiation source 29, emitting radiation to a mamma from the radiation source 29 in a case where the radiation source 29 reaches each imaging position, and performing imaging using the radiation detector 11 in synchronization with a timing of the emission may be used.

Next, a configuration of the radiation image capturing system 1 that includes the mammography apparatus 10 of the embodiment will be described. The radiation image capturing system 1 of the embodiment has a function of performing capturing of a radiation image through an operation of a user such as a doctor or a radiation technician, on the basis of an instruction (imaging menu) input from an external system (for example, radiology information system (RIS)) through the console 6. In the embodiment, the technician, the doctor, or the like who performs imaging using the radiation image capturing system 1 (mammography apparatus 10) is referred to as a "user".

Figure 3:
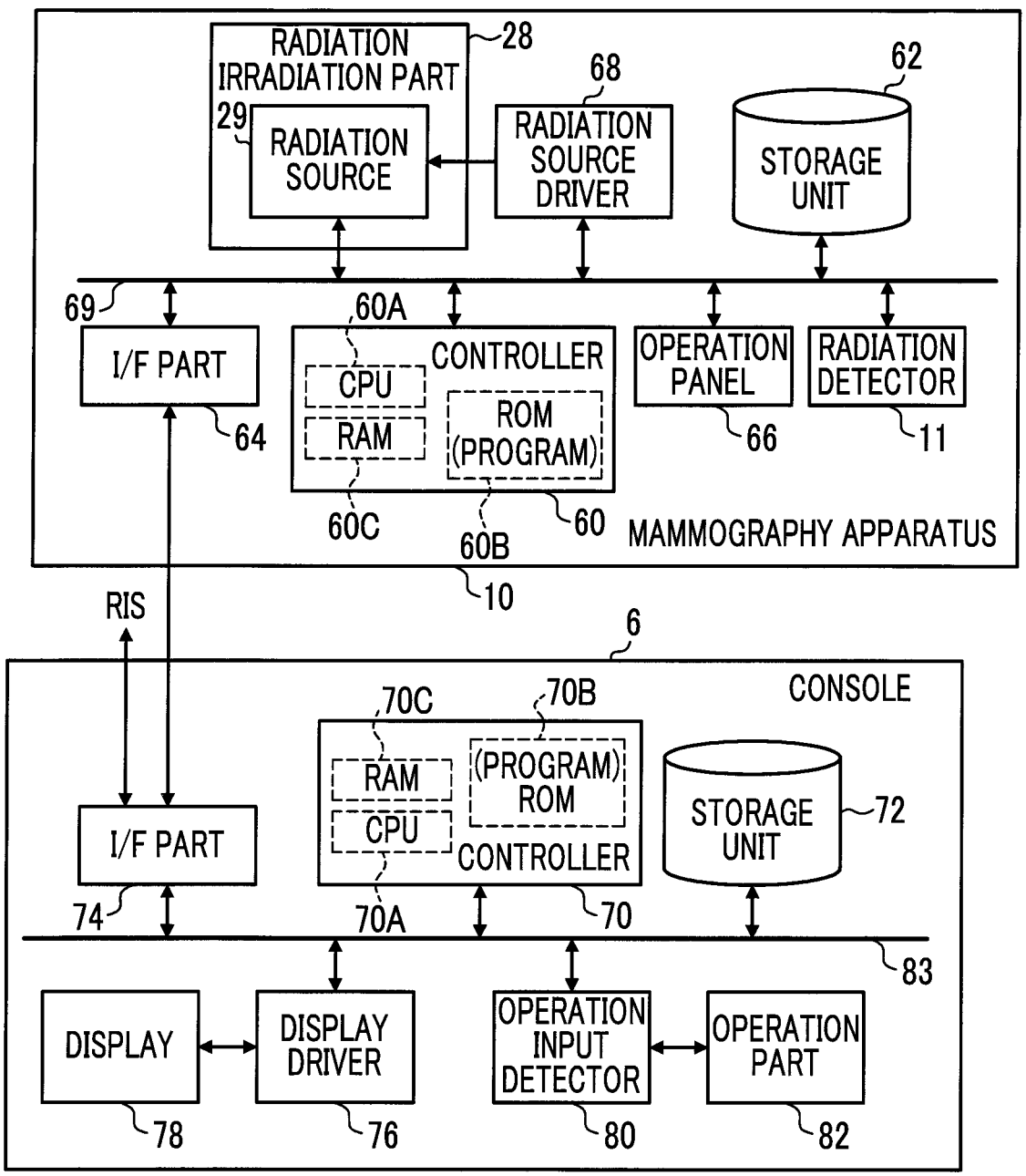
FIG. 3 is a block diagram showing an example of a configuration of a radiation image capturing system according to the first embodiment.

FIG. 3 is a block diagram showing an example of the configuration of the radiation image capturing system 1 of the embodiment. As shown in FIG. 3, the radiation image capturing system 1 of the embodiment includes the mammography apparatus 10 and the console 6.

The console 6 controls the mammography apparatus 10 using an imaging menu acquired from an external system or the like through a wireless communication local area network (LAN) or the like, a variety of other information, and the like.

The console 6 of the embodiment is a server computer, for example. As shown in FIG. 3, the console 6 includes a controller 70, a storage unit 72, an interface (I/F) part 74, a display driver 76, a display 78, an operation input detector 80, and an operation part 82. The controller 70, the storage unit 72, the I/F part 74, the display driver 76, and the operation input detector 80 are connected to each other to be able to exchange a variety of information through a bus 83 such as a system bus or a control bus.

The controller 70 of the embodiment controls the entire operation of the console 6. The controller 70 of the embodiment includes a central processing unit (CPU) 70A, a read only memory (ROM) 70B, and a random access memory (RAM) 70C. Various programs and the like that are executed by the CPU 70A and include an image display processing program (to be described below) are stored in advance in the ROM 70B. The RAM 70C temporarily stores a variety of data. The controller 70 of the embodiment is an example of an image generation unit and a deriving unit of the present disclosure.

The storage unit 72 stores image data of a radiation image captured by the mammography apparatus 10, a variety of other information, and the like. Specific examples of the storage unit 72 include a hard disk drive (HDD), a solid state drive (SSD) and the like.

The I/F part 74 performs communication of a variety of information with the mammography apparatus 10 or an external system such as an RIS through wireless communication or wired communication.

The display 78 displays a variety of information. The display driver 76 controls display of a variety of information on the display 78.

The operation part 82 is used for a user to input an instruction relating to the capturing or the like of a radiation image including a radiation exposure instruction, a variety of information, and the like.

The operation part 82 is not particularly limited, and for example, a variety of switches, a touch panel, a touch pen, a mouse, and the like are exemplified. The operation part 82 and the display 78 may be integrally used as a touch panel display. The operation input detector 80 detects an operation state with respect to the operation part 82.

On the other hand, as shown in FIG. 3, the mammography apparatus 10 of the embodiment includes the radiation detector 11, the radiation irradiation part 28, a controller 60, a storage unit 62, an I/F part 64, an operation panel 66, and a radiation source driver 68.

The radiation detector 11, the radiation irradiation part 28, the controller 60, the storage unit 62, the I/F part 64, the operation panel 66, and the radiation source driver 68 are connected to each other to be able to exchange a variety of information through a bus 69 such as a system bus or a control bus.

The controller 60 of the embodiment controls the entire operation of the mammography apparatus 10. Further, the controller 60 of the embodiment controls the radiation detector 11 and the radiation irradiation part 28 in a case where capturing of a radiation image is performed. The controller 60 of the embodiment includes a CPU 60A, a ROM 60B, and a RAM 60C. Various programs and the like that are executed by the CPU 60A and include an imaging processing program (to be described below) are stored in advance in the ROM 60B. The RAM 60C temporarily stores a variety of data.

As shown in FIG. 3, as described above, the radiation irradiation part 28 includes the radiation source 29. The radiation source driver 68 rotates a shaft (not shown) provided in the above-described imaging part 12 to continuously move the radiation source 29 of the radiation irradiation part 28, to thereby change an incidence angle of radiation.

The storage unit 62 stores image data of a radiation image captured by the radiation detector 11, a variety of other information, and the like. Specific examples of the storage unit 62 include an HDD, an SSD, and the like.

The I/F part 64 performs communication of a variety of information with the console 6 through wireless communication or wired communication.

The operation panel 66 is provided on the imaging stand 16 of the mammography apparatus 10, for example, as a plurality of switches. The operation panel 66 may be provided as a touch panel.

Figure 4:
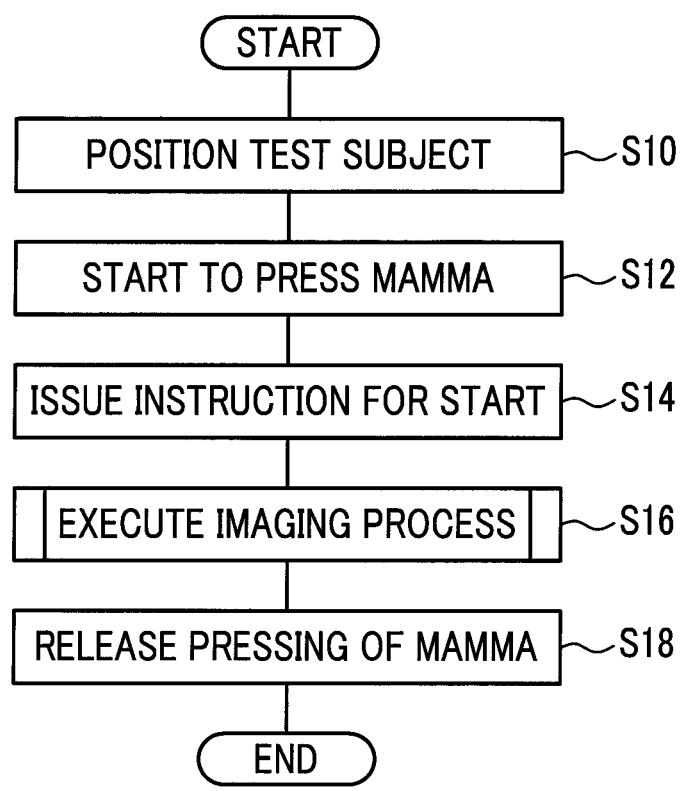
FIG. 4 is a flowchart showing an example of a flow of the entire imaging by the mammography apparatus according to the first embodiment.

Next, operations of the radiation image capturing system 1 and the mammography apparatus 10 of the embodiment will be described with reference to the drawings. First, the entire flow of capturing a radiation image of a mamma by the radiation image capturing system 1 of the embodiment will be described. FIG. 4 shows a flowchart showing an example of the entire flow of capturing a radiation image by the radiation image capturing system 1 of the embodiment.

In step S10, the user positions the mamma of the test subject on the imaging surface 24 of the imaging stand 16 of the mammography apparatus 10.

Then, in step S12, the user starts to press the mamma by using the pressing plate 20. In this manner, by pressing the mamma between the imaging stand 16 and the pressing plate 20, the mamma is fixed and made thin to have a uniform thickness. In a case where contrast imaging, specifically, dual imaging or combination imaging is performed, administration of the contrast medium is performed before pressing the mamma by using the pressing plate 20, at a timing in which time for the contrast medium to reach a lesion (blood vessels in the lesion) in the mamma is taken into consideration.

In step S14, the user issues an instruction for the start of capturing a radiation image from the operation part 82 of the console 6. The instruction for the start of imaging (imaging start instruction) is transmitted to the mammography apparatus 10 through the I/F part 74. In addition, in the radiation image capturing system 1 of the embodiment, the imaging menu is also transmitted to the mammography apparatus 10 from the console 6 through the I/F part 74.

Next, in step S16, the mammography apparatus 10 executes an imaging process, which will be described in detail later, (refer to FIG. 5) and captures a radiation image of the mamma. In this manner, the mammography apparatus 10 of the embodiment executes the imaging process shown in FIG. 5, which will be described in detail below, in a case where the imaging start instruction of a radiation image and the imaging menu are received from the console 6.

In step S18, the user moves the pressing plate 20 in a direction in which the pressing plate 20 becomes distant from the imaging stand 16 to release the pressing of the mamma by the pressing plate 20 and ends the capturing of the radiation image.

Figure 5:
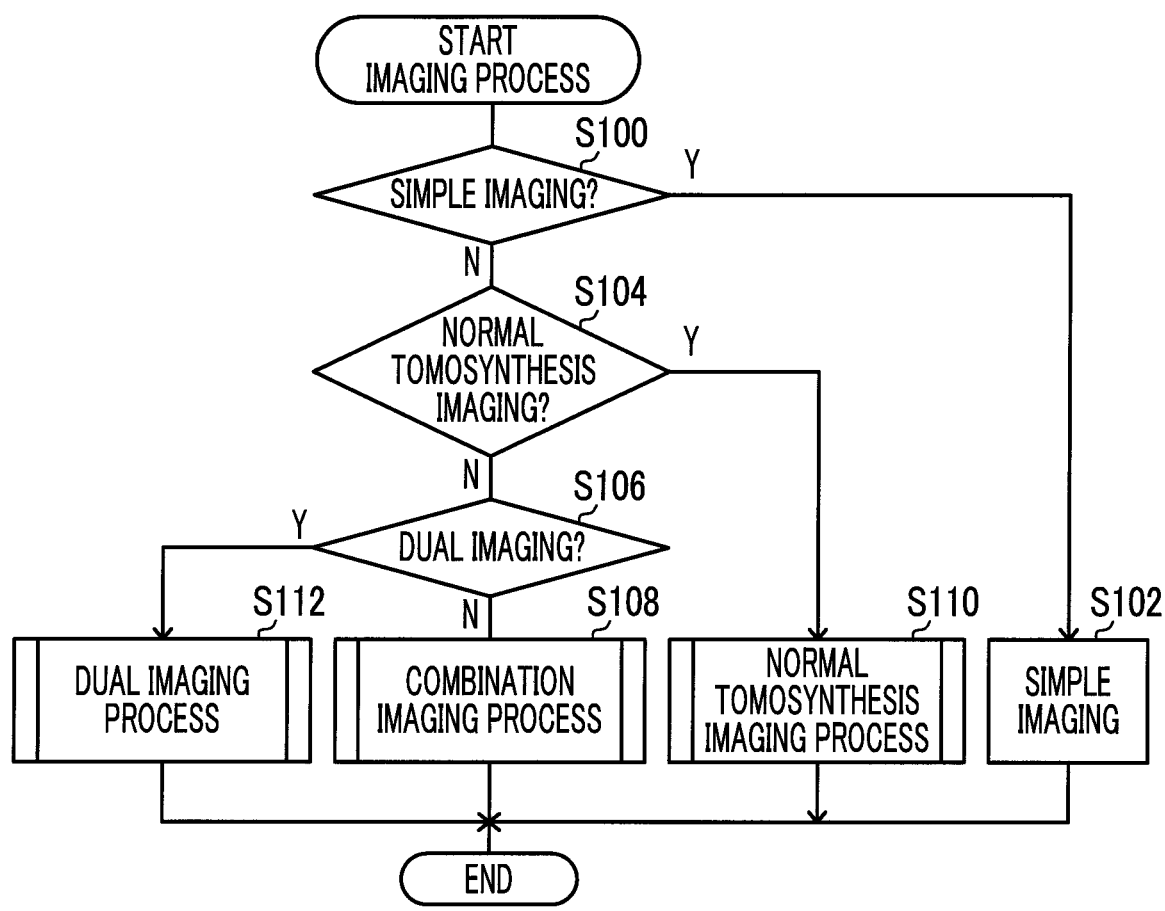
FIG. 5 is a flowchart showing an example of a flow of an imaging process executed by the mammography apparatus according to the first embodiment.

Next, the above-described imaging process executed by the mammography apparatus 10 of the embodiment will be described. FIG. 5 shows a flowchart showing an example of a flow of the imaging process executed by the controller 60 of the mammography apparatus 10 of the embodiment. In the mammography apparatus 10 of the embodiment, the CPU 60A of the controller 60 executes the imaging processing program stored in the ROM 60B to execute the imaging process shown in FIG. 5. The imaging processing program of the embodiment is an example of the control program of the present disclosure.

In step S100, the controller 60 determines whether the imaging mode instructed by the imaging menu is simple imaging. In a case where the instructed imaging mode is simple imaging, the determination in step S100 is affirmative and the process proceeds to step S102.

In step S102, the controller 60 emits radiation from the radiation source 29 of the radiation irradiation part 28 to perform imaging (simple imaging) of the mamma of the test subject according to the imaging menu, and then ends the present imaging process. Here, the specific method for performing simple imaging is not particularly limited, and a general method of performing simple imaging may be applied.

In a case where the simple imaging in step S102 is ended, the captured radiation image is output to the console 6 from the mammography apparatus 10. Hereinafter, the radiation image captured in the simple imaging is referred to as a "simple radiation image". In the embodiment, in a case where the radiation image captured by the mammography apparatus 10 is collectively referred to regardless of the type of imaging or the like, the image is simply referred to as the "radiation image".

On the other hand, in a case where the imaging mode instructed by the imaging menu is not simple imaging, the determination in step S100 is negative and the process proceeds to step S104. In step S104, the controller 60 determines whether the instructed imaging mode is normal tomosynthesis imaging. In a case where the instructed imaging mode is not normal tomosynthesis imaging, the determination in step S104 is negative and the process proceeds to step S106.

In step S106, the controller 60 determines whether the instructed imaging mode is dual imaging. In a case where the instructed imaging mode is not dual imaging, the determination in step S106 is negative and the process proceeds to step S108.

In step S108, the controller 60 performs a combination imaging process, which will be described in detail below, (refer to FIG. 8) for performing combination imaging, and then ends the present imaging process.

Figure 6:
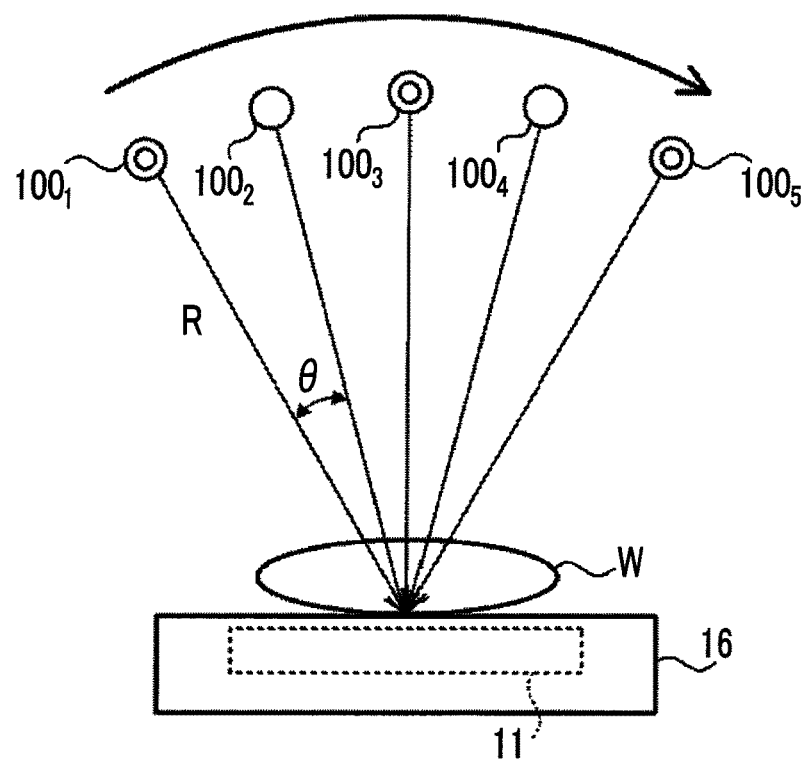
FIG. 6 is a diagram for describing an example of imaging positions of combination imaging.

Here, combination imaging of the embodiment will be described. FIG. 6 shows an example of imaging positions of combination imaging in which both the normal tomosynthesis imaging, in which imaging is performed by emitting radiation R to a mamma W from the radiation source 29 at each of five imaging positions $100_1$, $100_2$, $100_3$, $100_4$, and $100_5$ of which the incidence angles are different, and the dual imaging, in which imaging is performed by emitting radiation R to the mamma W from the radiation source 29 at each of three imaging positions $100_1$, $100_3$, and $100_5$ of which the incidence angles are different, are performed.

As described above, in case of performing dual imaging, two times of imaging, that is, imaging in which radiation R with low energy is emitted (hereinafter, referred to as "LE imaging") and imaging in which radiation R with high energy is emitted (hereinafter, referred to as "HE imaging") are performed at one imaging position.

In the embodiment, since the dual imaging is applied to the contrast imaging as described above, the low energy refers to energy lower than the k absorption end of the iodine contrast medium and the high energy refers to energy higher than the k absorption end of the iodine contrast medium. In the mammography apparatus 10 of the embodiment, the energy of the radiation R to be emitted from the radiation source 29 is adjusted by the tube voltage applied to the radiation source 29, and the energy of the radiation R to be emitted becomes high as the tube voltage of the radiation source 29 is increased.

In the mammography apparatus 10 of the embodiment, the energy of the radiation R emitted in the LE imaging is made equal to the energy of the radiation R emitted in the normal tomosynthesis imaging. In this manner, in the embodiment, a radiation image captured in the LE imaging of the dual imaging can be used as a captured image obtained by the normal tomosynthesis imaging.

In the example shown in FIG. 6, as described above, the three imaging positions $100_1$, $100_3$, and $100_5$ are the imaging positions of the dual imaging, and the five imaging positions $100_1$, $100_2$, $100_3$, $100_4$, and $100_5$ are the imaging positions of the normal tomosynthesis imaging. Therefore, the mammography apparatus 10 performs the LE imaging and the HE imaging at the imaging positions $100_1$, $100_3$, and $100_5$ and performs only LE imaging at the imaging positions $100_2$ and $100_4$.

As an example, in the mammography apparatus 10 of the embodiment, the imaging positions of the radiation source 29 in case of performing the normal tomosynthesis imaging and the imaging positions of the radiation source 29 in case of performing the dual imaging are determined in advance. Further, as an example, in the mammography apparatus 10 of the embodiment, the imaging positions of the radiation source 29 where only LE imaging of the combination imaging is performed and the imaging positions of the radiation source 29 where the dual imaging (LE imaging and HE imaging) is perform are determined in advance. These imaging positions may be set by a user.

In addition, in the mammography apparatus 10 of the embodiment, at the imaging positions $100_2$ and $100_4$ where only LE imaging is performed, the LE imaging is performed by emitting radiation R to the mamma W in a state where the radiation source 29 is moved (without being stopped). Meanwhile, at the imaging positions $100_1$, $100_3$, and $100_5$ where the dual imaging is performed, the LE imaging and the HE imaging are sequentially and continuously performed by emitting radiation R to the mamma W in a state where the movement of the radiation source 29 is stopped.

Since, at the imaging position where only LE imaging is performed, the LE imaging is performed in a state where the radiation source 29 is moved, as an example, in the embodiment, an irradiation time (first irradiation time) during which radiation R is emitted from the radiation source 29 is set to be shorter than an irradiation time (second irradiation time) during which radiation R is emitted from the radiation source 29 in each of the LE imaging and the HE imaging of the dual imaging. In this manner, it is possible to reduce a blur generated in a radiation image captured in the LE imaging due to the movement of the radiation source 29, and to reduce time until the imaging is completed. As an example, in the embodiment, the second irradiation time during which radiation R is emitted from the radiation source 29 in the LE imaging of the dual imaging and the second irradiation time during which radiation R is emitted from the radiation source 29 in the HE imaging of the dual imaging are the same as each other. A specific example of such a first irradiation time is 100 msec or less. Further, a specific example of the second irradiation time is 500 msec to 1 sec.

The energy (low energy) of the radiation R to be emitted in the LE imaging of the embodiment corresponds to an example of first energy of the present disclosure, and the energy (high energy) of the radiation R to be emitted in the HE imaging of the embodiment corresponds to an example of second energy of the present disclosure. The LE imaging of the embodiment corresponds to an example of first imaging of the present disclosure, and the HE imaging of the embodiment corresponds to an example of second imaging of the present disclosure. Further, the imaging position where only the LE imaging of the combination imaging of the embodiment is performed corresponds to an example of a first imaging position of the present disclosure, and the imaging position where the dual imaging of the embodiment is performed corresponds to an example of a second imaging position of the present disclosure.

Figure 7:
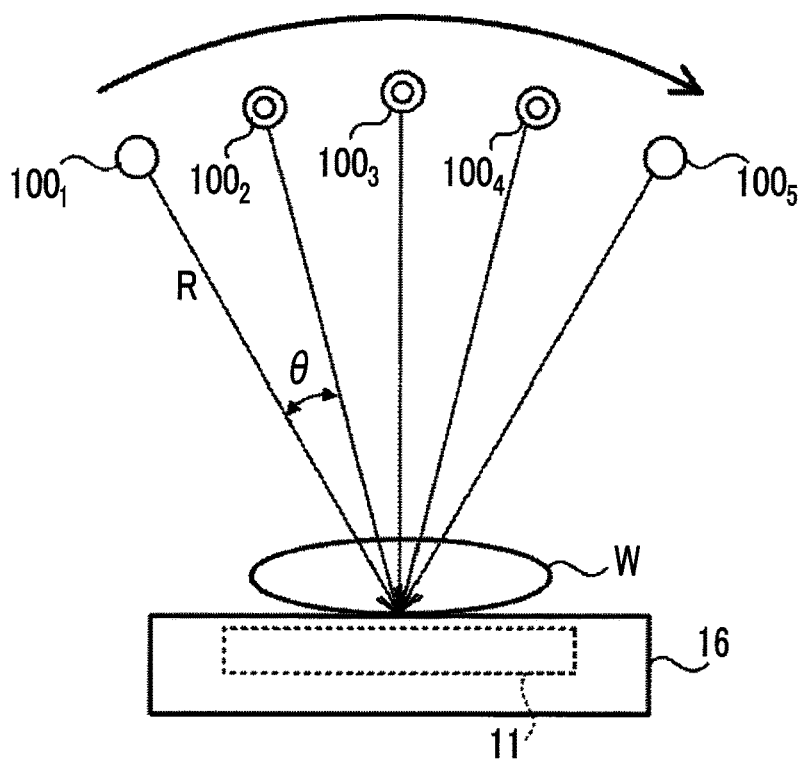
FIG. 7 is a diagram for describing another example of imaging positions of combination imaging.

The imaging position of the combination imaging is not limited to the imaging positions shown in FIG. 6. FIG. 7 shows another example of imaging positions of the combination imaging. In the example shown in FIG. 7, three imaging positions $100_2$, $100_3$, and $100_4$ are the imaging positions of the dual imaging, and five imaging positions $100_1$, $100_2$, $100_3$, $100_4$, and $100_5$ are the imaging positions of the normal tomosynthesis imaging. Therefore, the mammography apparatus 10 performs the LE imaging and the HE imaging at the imaging positions $100_2$, $100_3$, and $100_4$ and performs only LE imaging at the imaging positions $100_1$ and $100_5$.

The number of times of imaging (number of imaging positions) in the normal tomosynthesis imaging and the number of times of imaging (number of imaging positions) in the dual imaging included in the combination imaging, incidence angles of radiation, and the like are not limited to those described in the embodiment.

Figure 8:
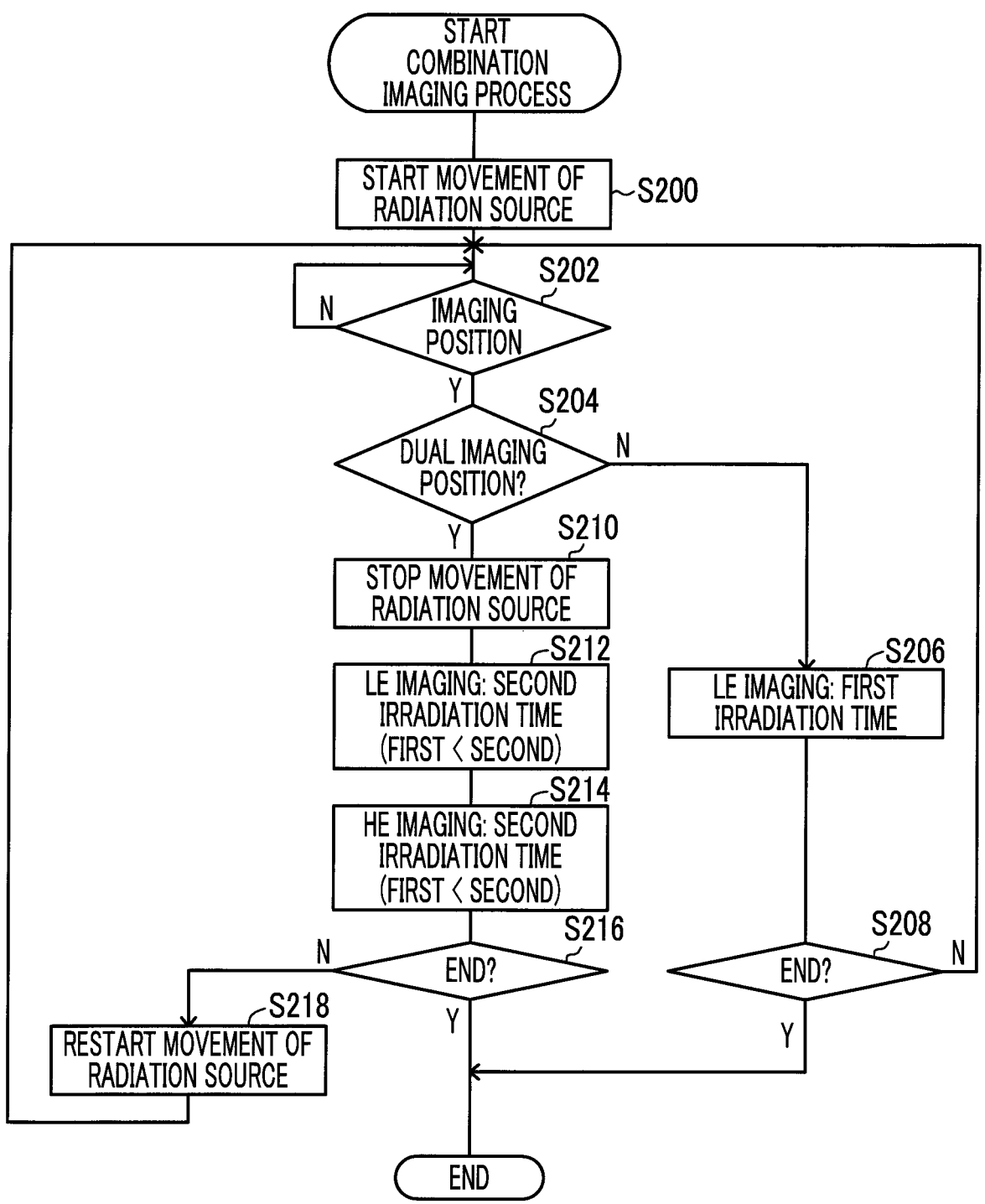
FIG. 8 is a flowchart showing an example of a flow of a combination imaging process in the imaging process according to the first embodiment.

FIG. 8 shows a flowchart of an example of the combination imaging process executed by the controller 60 of the embodiment.

In step S200 shown in FIG. 8, the controller 60 starts to move the radiation source 29 (radiation irradiation part 28) by using the radiation source driver 68.

Next, in step S202, the controller 60 determines whether the radiation source 29 has reached the imaging position. In step S202, the negative determination is repeated until the radiation source 29 reaches the imaging position, and in a case where the radiation source 29 has reached the imaging position, the determination is affirmative, and the process proceeds to step S204.

In step S204, the controller 60 determines whether the reached imaging position is an imaging position where the dual imaging is performed. In a case where the reached imaging position is not an imaging position where the dual imaging is performed, that is, in a case where the reached imaging position is an imaging position where only the LE imaging is performed, the determination in step S204 is negative, and the process proceeds to step S206.

In step S206, the controller 60 emits radiation R with low energy from the radiation source 29 with the irradiation time as the first irradiation time to perform the LE imaging. In this case, as described above, the LE imaging is performed by emitting radiation R from the radiation source 29 in a state where the radiation irradiation part 28 is moved. In a case where the filter positioned within the irradiation field is not the Rh filter 42 (which is the Cu filter 44), the controller 60 positions the Rh filter 42 within the irradiation field by moving the Rh filter 42 and the Cu filter 44.

The radiation image captured in the LE imaging by the radiation detector 11 is output to the console 6 from the mammography apparatus 10. Hereinafter, the radiation image captured in the LE imaging is referred to as a "first radiation image".

In step S208, the controller 60 determines whether to end the present combination imaging process. In a case where the imaging position is the last imaging position of the entire combination imaging (for example, imaging position $100_5$ in FIG. 7), the determination in step S208 is affirmative so that the present combination imaging process is ended, and the imaging process (refer to FIG. 5) is ended. Meanwhile, in a case where the imaging position is not the last imaging position, the determination in step S208 is negative, and the process returns to step S202.

In the determination in step S204 described above, in a case where the reached imaging position is an imaging position where the dual imaging is performed, the determination is affirmative, and the process proceeds to step S210.

In step S210, the controller 60 stops the movement of the radiation source 29 at the imaging position where the dual imaging is performed.

In step S212, the controller 60 emits radiation R with low energy from the radiation source 29 with the irradiation time as the second irradiation time to perform the LE imaging. That is, in the present step, unlike step S206 described above, the LE imaging is performed by emitting radiation R from the radiation source 29 in a state where the movement of the radiation source 29 is stopped. In a case where the filter positioned within the irradiation field is not the Rh filter 42 (which is the Cu filter 44), the controller 60 positions the Rh filter 42 within the irradiation field by moving the Rh filter 42 and the Cu filter 44.

The first radiation image captured in the LE imaging by the radiation detector 11 is output to the console 6 from the mammography apparatus 10.

Further, in step S214, the controller 60 emits radiation R with high energy from the radiation source 29 with the irradiation time as the second irradiation time in a state where the movement of the radiation source 29 is stopped, to perform the HE imaging. In the embodiment, in a case where the energy of the radiation R to be emitted from the radiation source 29 is changed from low energy to high energy, the controller 60 changes the tube voltage according to the high energy by increasing the tube voltage to be applied to the radiation source 29. In addition, the controller 60 positions the Cu filter 44 within the irradiation field by moving the Rh filter 42 and the Cu filter 44.

In the embodiment, a dose of the radiation R emitted in the LE imaging is the same as a dose of the radiation R emitted in the HE imaging. The "dose" in the embodiment refers to the mAs value and is represented by a value obtained by multiplying the tube current value and the irradiation time.

The radiation image captured in the HE imaging by the radiation detector 11 is output to the console 6 from the mammography apparatus 10. Hereinafter, the radiation image captured in the HE imaging is referred to as a "second radiation image".

In the dual imaging of the embodiment, an aspect in which the HE imaging is performed after the LE imaging is performed in this manner has been described, the order of the LE imaging and the HE imaging is not particularly limited, and the LE imaging may be performed after the HE imaging is performed.

In step S216, the controller 60 determines whether to end the present combination imaging process. In a case where the imaging position is the last imaging position of the entire combination imaging (for example, imaging position $100_5$ in FIG. 6), the determination in step S216 is affirmative so that the present combination imaging process is ended, and the imaging process (refer to FIG. 5) is ended. Meanwhile, in a case where the imaging position is not the last imaging position, the determination in step S216 is negative, and the process proceeds to step S218.

In step S218, after the controller 60 restarts the movement of the radiation source 29, the process returns to step S202, and the processes in the above-described steps are repeated.

In the combination imaging process of the embodiment, an aspect in which the captured radiation image is output to the console 6 whenever each of the LE imaging in step S206, the LE imaging in step S212, and the HE imaging in step S214 is ended has been described, but the timing at which the radiation image is output to the console 6 is not limited. For example, an aspect may be adopted in which the captured radiation image is stored in the storage unit 62 until the combination imaging process is ended, and the controller 60 reads all the radiation images captured in the combination imaging process from the storage unit 62 and outputs the read radiation images to the console 6 according to a timing at which the combination imaging process is ended.

On the other hand, in a case where the imaging mode instructed by the imaging menu is normal tomosynthesis imaging, the determination in step S104 of the imaging process is affirmative and the process proceeds to step S110. In step S110, in order to perform the normal tomosynthesis imaging, the controller 60 performs the normal tomosynthesis imaging process and then ends the present imaging process.

Figure 9:
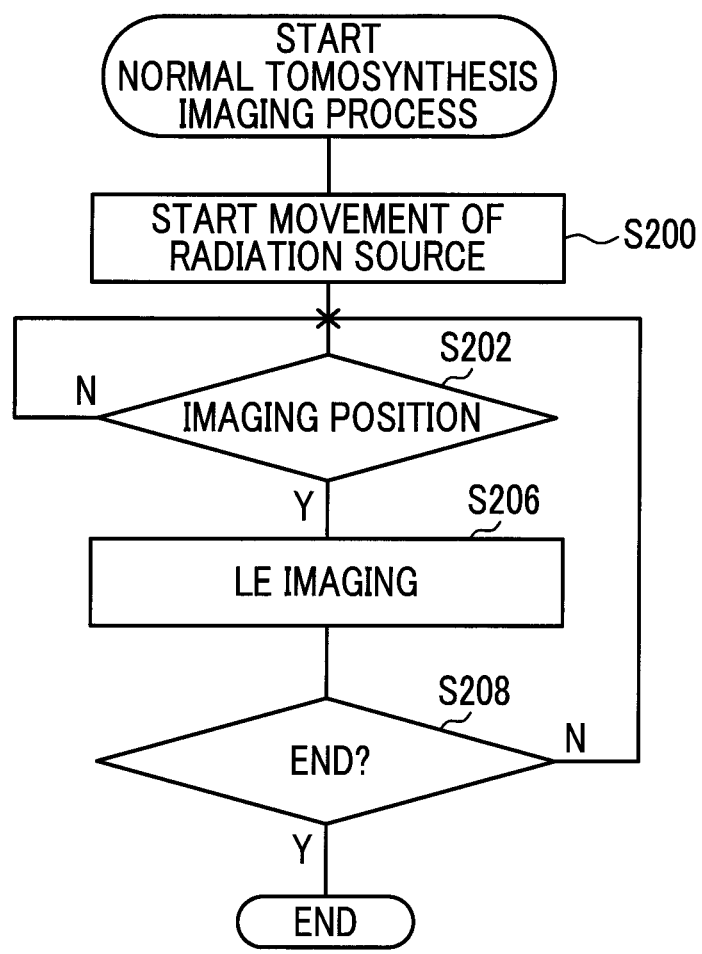
FIG. 9 is a flowchart showing an example of a flow of a normal tomosynthesis imaging process in the imaging process according to the first embodiment.

FIG. 9 shows a flowchart of an example of the normal tomosynthesis imaging process executed by the controller 60 of the embodiment. As shown in FIG. 9, in the normal tomosynthesis imaging process in the embodiment, each process of steps S200, S202, S206, and S208 of the above-described combination imaging process (refer to FIG. 8) is performed. That is, in a case where the radiation source 29 is moved to reach the imaging position, the controller 60 repeats the process of performing the LE imaging in a state where the radiation source 29 is moved, until the last imaging position. The first radiation image captured in the normal tomosynthesis imaging process by the radiation detector 11 is output to the console 6 from the mammography apparatus 10.

On the other hand, in a case where the imaging mode instructed by the imaging menu is dual imaging, the determination in step S106 of the imaging process is affirmative and the process proceeds to step S112. In step S112, the controller 60 performs the dual imaging process, and then ends the present imaging process.

Figure 10:
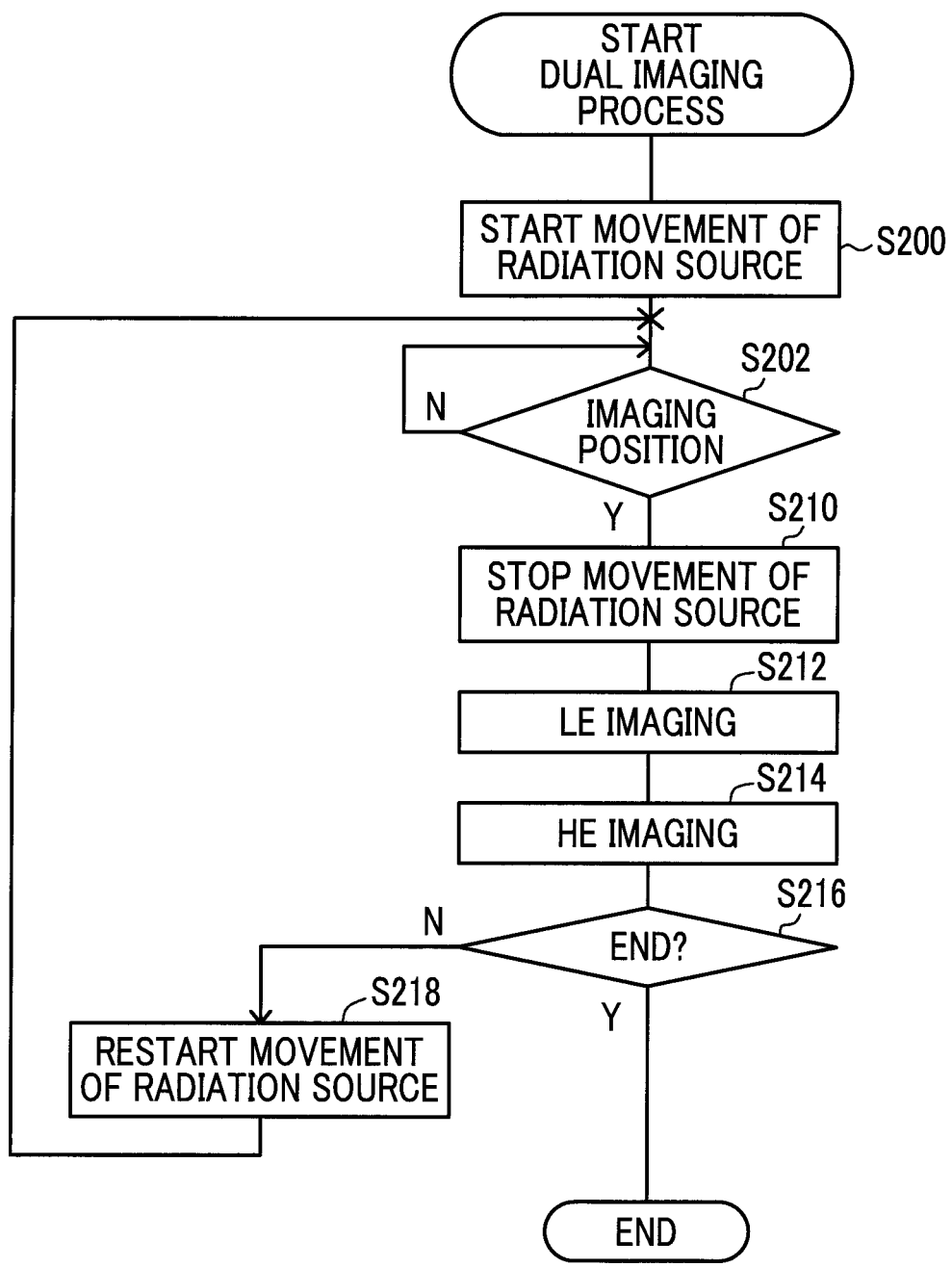
FIG. 10 is a flowchart showing an example of a flow of a dual imaging process in the imaging process according to the first embodiment.

FIG. 10 shows a flowchart of an example of the dual imaging process executed by the controller 60 of the embodiment. As shown in FIG. 10, in the dual imaging process in the embodiment, each process of steps S200, S202, S210, S212, S214, S216, and S218 of the above-described combination imaging process (refer to FIG. 8) is performed. That is, in a case where the radiation source 29 is moved to reach the imaging position, the controller 60 repeats the process of performing the LE imaging and the HE imaging in a state where the movement of the radiation source 29 is stopped and of starting the movement of the radiation source 29 again, until the last imaging position. The first radiation image and the second radiation image captured in the dual imaging process by the radiation detector 11 are output to the console 6 from the mammography apparatus 10.

Figure 11:
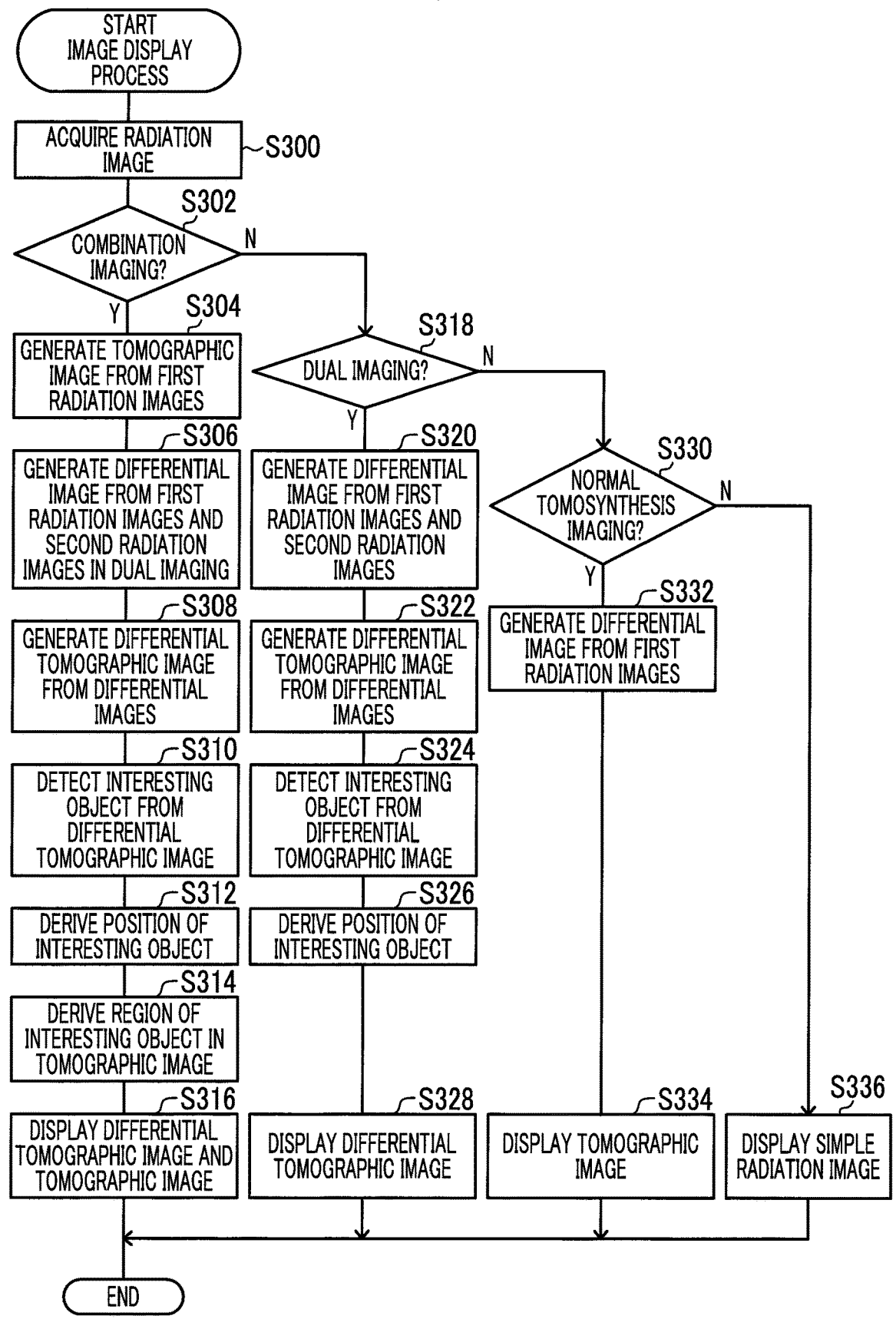
FIG. 11 is a flowchart showing an example of a flow of an image display process executed by a console according to the first embodiment.

In a case where the console 6 receives the radiation images captured in this manner from the mammography apparatus 10, the received radiation images are stored in the storage unit 72 and displayed on the display 78. The timing at which the console 6 displays the radiation image is not particularly limited, and for example, the display of the radiation image may be performed according to the user's instruction or performed at any time according to the capturing of the radiation image by the mammography apparatus 10. FIG. 11 shows a flowchart showing an example of a flow of the image display process executed by the controller 70 of the console 6 of the embodiment. In the console 6 of the embodiment, the CPU 70A of the controller 70 executes an image display processing program stored in the ROM 70B to execute the image display process shown in FIG. 11. The image display processing program of the embodiment is an example of the image processing program of the present disclosure.

In step S300 shown in FIG. 11, the controller 70 acquires the radiation image for display from the storage unit 72.

In step S302, the controller 70 determines whether the acquired radiation image is a radiation image captured in the combination imaging. In a case where the radiation image captured in the combination imaging, that is, the radiation image captured in the combination imaging process (refer to FIG. 8) is acquired, the determination in step S302 is affirmative and the process proceeds to step S304.

In step S304, the controller 70 generates a tomographic image from a plurality of first radiation images captured in the LE imaging, among the acquired radiation images. As an example, the controller 70 of the embodiment performs, on the first radiation image, a predetermined image process such as a scattered ray removal process for removing scattered ray components, or a radiation quality correction process for adjusting the contrast of the mamma W. Thereafter, the controller 70 calculates a movement amount of an interesting object between the plurality of first radiation images on the basis of the incidence angle of the radiation R at each imaging position where the first radiation image is captured, and reconstructs a tomographic image on the basis of a known reconstruction method. The reconstruction method is not limited, and as the reconstruction method, an algebraic reconstruction method, a successive approximation reconstruction method, and the like can be used in addition to a computed tomography (CT) reconstruction method such as a back projection method, a shift addition method, and a filtered back projection (FBP) method.

The slice thickness of a tomographic image to be generated is random, may be a predetermined thickness, or may be a thickness instructed by the user. In addition, the number of tomographic images to be generated is set in advance, and the slice thickness may be set according to the thickness of the mamma W in a state where the mamma W are pressed by the pressing plate 20 and the number of tomographic images to be generated.

In step S306, the controller 70 generates a differential image for each imaging position from a plurality of first radiation images and second radiation images in the dual imaging. The controller 70 of the embodiment generates image data of the differential image in which the administered contrast medium is emphasized, by subtracting, for each corresponding pixel, image data, which is obtained by multiplying a first coefficient set in advance according to the contrast medium to image data of the first radiation image in the dual imaging, from image data, which is obtained by multiplying a second coefficient set in advance according to the contrast medium to image data of the second radiation image. The method of generating the differential image by the controller 70 is not limited thereto, and a known method of generating a differential image may be used.

In step S308, the controller 70 generates a differential tomographic image from a plurality of generated differential images. The method of generating the differential tomographic image is not limited. The method may be the same as or different from the method of generating a tomographic image in step S304. In the generation of the differential tomographic image, the controller 70 may perform the image process for emphasizing the administered contrast medium.

In step S310, the controller 70 detects a region of an interesting object (region of interest: ROI) from the plurality of differential tomographic images. The "interesting object" refers to a target or the like that the user observes or the like, and in the embodiment, refers to a portion of a lesion in the mamma W in which a contrast medium has been administered. The method of detecting the ROI from the differential tomographic image is not particularly limited, and may be a method according to features of the ROI to be detected. In the embodiment, as described above, an image of a lesion in the mamma W in which the contrast medium has been administered (hereinafter, referred to as a "contrast-medium image") is detected, but the contrast-medium image is a white image, that is, an image having a small pixel value, as compared with the tissue of the mamma W. Therefore, a region in which pixels of which the pixel value is smaller than a predetermined threshold are gathered equal to or more than a predetermined number (equal to or more than an area) can be detected as the ROI.

In step S312, the controller 70 derives a three-dimensional position of the detected ROI from the plurality of differential tomographic images. The method of deriving the position of the ROI from the differential tomographic image is not particularly limited. For example, a depth direction (direction in which the radiation R is emitted) may be derived from a slice position (depth) of the differential tomographic image in which the image of the ROI is included.

In step S314, the controller 70 derives a region corresponding to the region of the ROI from the plurality of tomographic images generated in step S304 on the basis of the position of the ROI derived in step S312.

In step S316, the controller 70 displays the generated differential tomographic image and tomographic image on the display 78 and then ends the present image display process.

Figure 12:
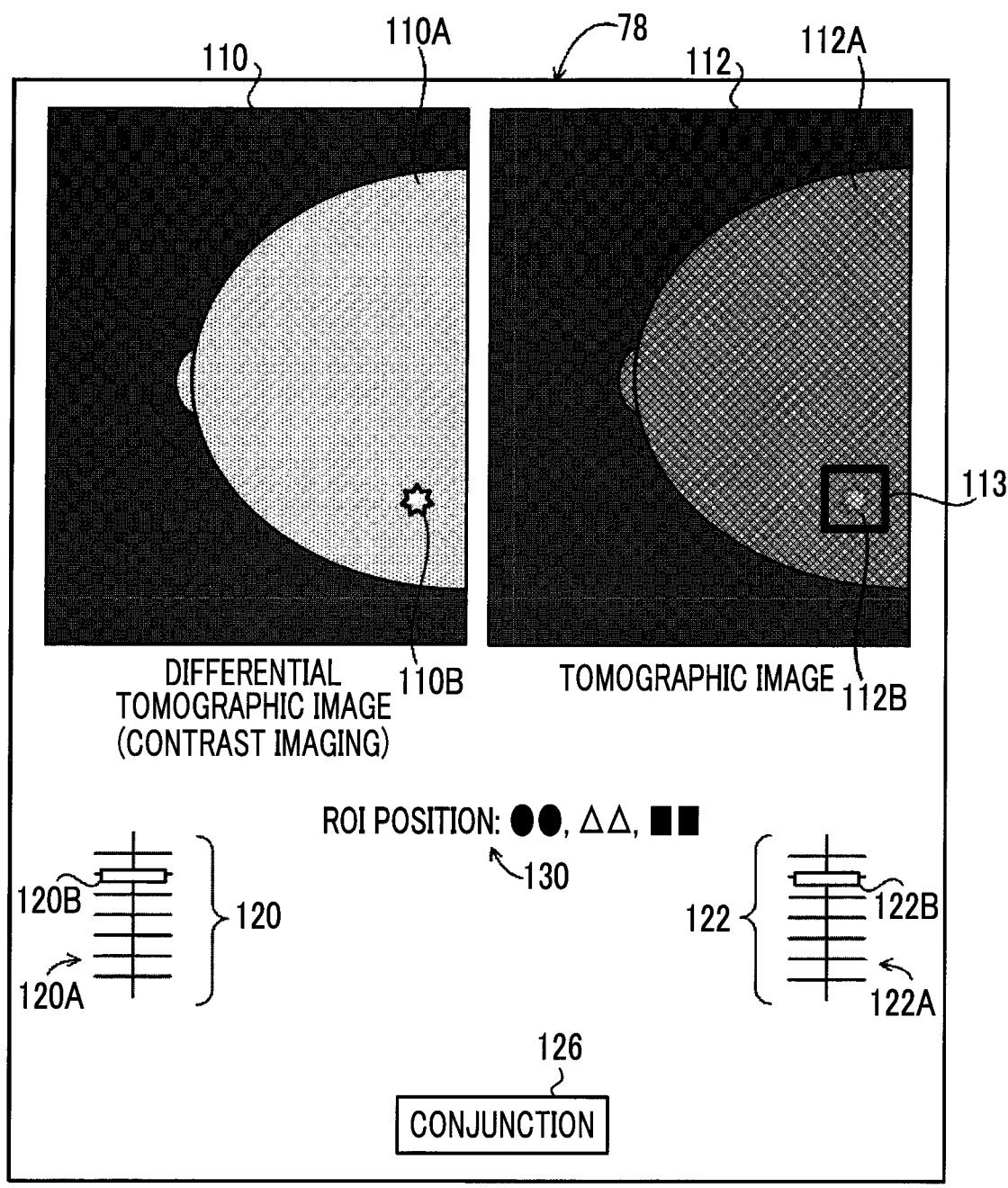
FIG. 12 is a diagram showing an example of a display state of a differential tomographic image and a tomographic image.

FIG. 12 shows an example of displaying a differential tomographic image and a tomographic image on the display 78. In the example shown in FIG. 12, an aspect in which the controller 70 displays a differential tomographic image 110 and a tomographic image 112 side by side on the display 78 is shown. In the differential tomographic image 110 shown in FIG. 12, a mamma 110A and a contrast medium 110B are shown, and in the tomographic image 112, a mamma 112A and a contrast medium 112B are shown. In a case where the region derived in step S314 is included in the displayed tomographic image 112, the controller 70 of the embodiment displays a mark 113 for emphasizing the derived region on the tomographic image 112. In general, in the tomographic image 112, the contrast medium 112B is difficult to see as compared with the differential tomographic image 110, but it becomes easy to confirm the position of the contrast medium 112B by displaying the mark 113 on the tomographic image 112 as described above. The mark 113 is not particularly limited as long as the mark can emphasize the derived region (position of the contrast medium 112B). For example, the mark 113 may be a frame line surrounding the derived region, may be an arrow or the like, or may be a mark including characters.

Further, as shown in FIG. 12, the controller 70 of the embodiment displays slice position information 120 indicating the slice position of the displayed differential tomographic image 110, slice position information 122 indicating the slice position of the displayed tomographic image 112, and a conjunction button 126 on the display 78. The slice position information 120 includes a bar 120A and a slider 120B, and the position of the bar 120A on the slider 120B represents the slice position of the displayed differential tomographic image 110. In the embodiment, the user operates the operation part 82 to move the slider 120B along the bar 120A, so that the controller 70 displays the differential tomographic image 110 of the slice position according to the position of the slider 120B on the display 78.

Similarly, the slice position information 122 includes a bar 122A and a slider 122B, and the position of the bar 122A on the slider 122B represents the slice position of the displayed tomographic image 112. In the embodiment, the user operates the operation part 82 to move the slider 122B along the bar 122A, so that the controller 70 displays the tomographic image 112 of the slice position according to the position of the slider 122B on the display 78.

In the embodiment, in a case where the user operates the conjunction button 126 by using the operation part 82, the slice positions of the differential tomographic image 110 and the tomographic image 112 displayed on the display 78 are changed in conjunction with each other. Specifically, in a case where the change of the slice position is instructed by either the slider 120B or the slider 122B, the controller 70 displays the differential tomographic image 110 and the tomographic image 112 according to the instructed slice position on the display 78.

In addition, as shown in FIG. 12, the controller 70 of the embodiment displays ROI position information 130 indicating the position of the derived ROI, on the display 78. In this manner, by displaying the ROI position information 130, it is possible to inform the user of the position of the living body to be collected in the lesion biopsy.

Figure 13:
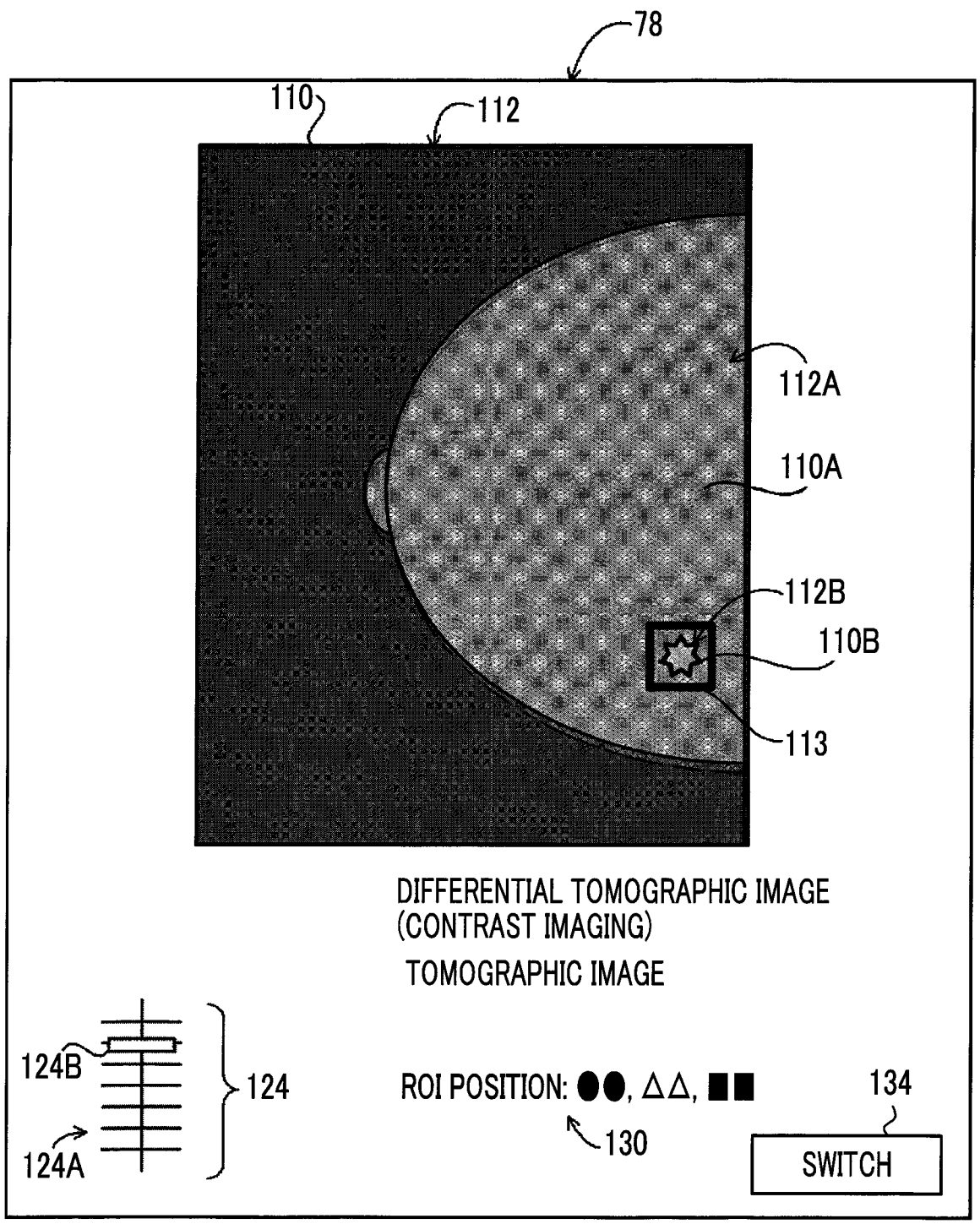
FIG. 13 is a diagram showing another example of a display state of a differential tomographic image and a tomographic image.

The method of displaying the differential tomographic image 110 and the tomographic image 112 on the display 78 is not limited to that shown in FIG. 12. For example, as shown in FIG. 13, the differential tomographic image 110 and the tomographic image 112 may be displayed in a superimposed manner on the display 78. In the example shown in FIG. 13, a state in which the differential tomographic image 110 of which the slice position is the same as the tomographic image 112 is displayed to be superimposed on the tomographic image 112 is shown. In the example shown in FIG. 13, the slice positions of the differential tomographic image 110 and the tomographic image 112 displayed on the display 78 are the same. In a case where the user operates the operation part 82 to move a slider 124B along a bar 124A of slice position information 124, the controller 70 displays the differential tomographic image 110 and the tomographic image 112 of the slice position according to the position of the slider 124B on the display 78. In addition, in the example shown in FIG. 13, the controller 70 further displays a switch button 134 on the display 78. In a case where the user operates the switch button 134 by using the operation part 82, the controller 70 displays the differential tomographic image 110 and the tomographic image 112 by switching the displayed differential tomographic image 110 and tomographic image 112 up and down (superimposed order).

For example, the display state of the differential tomographic image 110 and the tomographic image 112 displayed on the display 78 may be switched between a state of the example shown in FIG. 12 and a state of the example shown in FIG. 13 according to the user's instruction.

Meanwhile, in a case where the radiation image acquired for the display by the controller 70 in step S300 is not the radiation image captured in the combination imaging, the determination in step S302 is negative, and the process proceeds to step S318.

In step S318, the controller 70 determines whether the acquired radiation image is the first radiation image and the second radiation image captured in the dual imaging. In a case where the acquired radiation image is the first radiation image and the second radiation image captured in the dual imaging, that is, in a case where the acquired radiation image is the first radiation image and the second radiation image captured by the above-described dual imaging process (refer to FIG. 10), the determination in step S318 is affirmative and the process proceeds to step S320.

In step S320, similar to step S306, the controller 70 generates a differential image for each imaging position from the plurality of first radiation images and second radiation images. In step S322, similar to step S308, the controller 70 generates a differential tomographic image from the plurality of generated differential images. In step S324, similar to step S310, the controller 70 detects the ROI from the plurality of differential tomographic images. In step S326, similar to step S312, the controller 70 derives a three-dimensional position of the detected ROI from the plurality of differential tomographic images.

In step S328, the controller 70 displays the generated differential tomographic image on the display 78 and then ends the present image display process. The state in which the controller 70 displays the differential tomographic image on the display 78 is not particularly limited. For example, a state in which among the display shown in FIG. 12, only the differential tomographic image 110, the slice position information 120, and the ROI position information 130 are displayed on the display 78 may be adopted.

Meanwhile, in a case where the radiation image acquired for the display by the controller 70 in step S300 is not the radiation image captured in the dual imaging, the determination in step S318 is negative, and the process proceeds to step S330.

In step S330, the controller 70 determines whether the acquired radiation image is the first radiation image captured in the normal tomosynthesis imaging. In a case where the acquired radiation image is the first radiation image captured in the normal tomosynthesis imaging, that is, the first radiation image captured in the above-described normal tomosynthesis imaging process (refer to FIG. 9), the determination in step S330 is affirmative and the process proceeds to step S332.

In step S332, similar to step S304, the controller 70 generates a tomographic image from the plurality of first radiation images captured in the normal tomosynthesis imaging.

In step S334, the controller 70 displays the generated tomographic image on the display 78 and then ends the present image display process. The state in which the controller 70 displays the tomographic image on the display 78 is not particularly limited. For example, a state in which among the display shown in FIG. 12, only the tomographic image 112 and the slice position information 122 are displayed on the display 78 may be adopted. Even in this case, the ROI may be detected from the tomographic image and further the position of the ROI may be detected and displayed.

Meanwhile, in a case where the radiation image acquired for the display by the controller 70 is not the radiation image captured in the normal tomosynthesis imaging, the determination in step S330 is negative, and the process proceeds to step S336. In this case, the radiation image acquired by the controller 70 is a simple radiation image captured in the simple imaging in step S102 of the imaging process (refer to FIG. 5).

In step S336, the controller 70 displays the acquired simple radiation image on the display 78 and then ends the present image display process. Even in this case, the ROI may be detected from the simple radiation image and further the position of the ROI may be detected and displayed.

In this manner, in the mammography apparatus 10 of the embodiment, in the combination imaging, at the imaging position where only the LE imaging is performed, the first radiation image is captured by the radiation detector 11 by emitting the radiation R with low energy in a state where the radiation source 29 is moved. In addition, in the mammography apparatus 10 of the embodiment, in the combination imaging, at the imaging position where the dual imaging is performed, in a state where the movement of the radiation source 29 is stopped, the first radiation image is captured by the radiation detector 11 by emitting the radiation R with low energy and the second radiation image is captured by the radiation detector 11 by emitting the radiation R with high energy.

With the mammography apparatus 10 of the embodiment, at the imaging position where only the LE imaging is performed, the movement of the radiation source 29 is not stopped, and thus it is possible to further reduce the time required until the capturing of the first radiation image and the second radiation image is completed. Accordingly, since the time required for the combination imaging process is reduced, the time required for the imaging process (refer to FIG. 5) is reduced.

In case of capturing the radiation image, after the pressing of the mamma W is started in step S12 until the pressing of the mamma W is released in step S18 of FIG. 4 described above, the pressing of the mamma W by the pressing plate 20 is continued. In the mammography apparatus 10 of the embodiment, since it is possible to reduce the time required for the imaging process in step S16, it is possible to reduce the duration time for pressing the mamma W. In this manner, with the mammography apparatus 10 of the embodiment, it is possible to reduce a burden on the test subject.

In the mammography apparatus 10 of the embodiment, since the dual imaging is performed in a state where the movement of the radiation source 29 is stopped, it is possible to improve the image quality of the differential tomographic image generated from the first radiation image and the second radiation image captured in the dual imaging.

Second Embodiment

In the mammography apparatus 10 of the first embodiment described above, an aspect in which imaging is performed in a state where the movement of the radiation source 29 is stopped in the dual imaging of the combination imaging has been described. In contrast, in the mammography apparatus 10 of the embodiment, an aspect in which imaging is performed in a state where the radiation source 29 is moved in the dual imaging of the combination imaging.

Since the configuration of the mammography apparatus 10 is the same as in the first embodiment, description thereof will not be repeated. In the embodiment, since a partial process of the combination imaging process of the imaging process executed by the controller 60 of the mammography apparatus 10 is different from the combination imaging process (refer to FIG. 8) of the first embodiment, the different process will be described.

Figure 14:
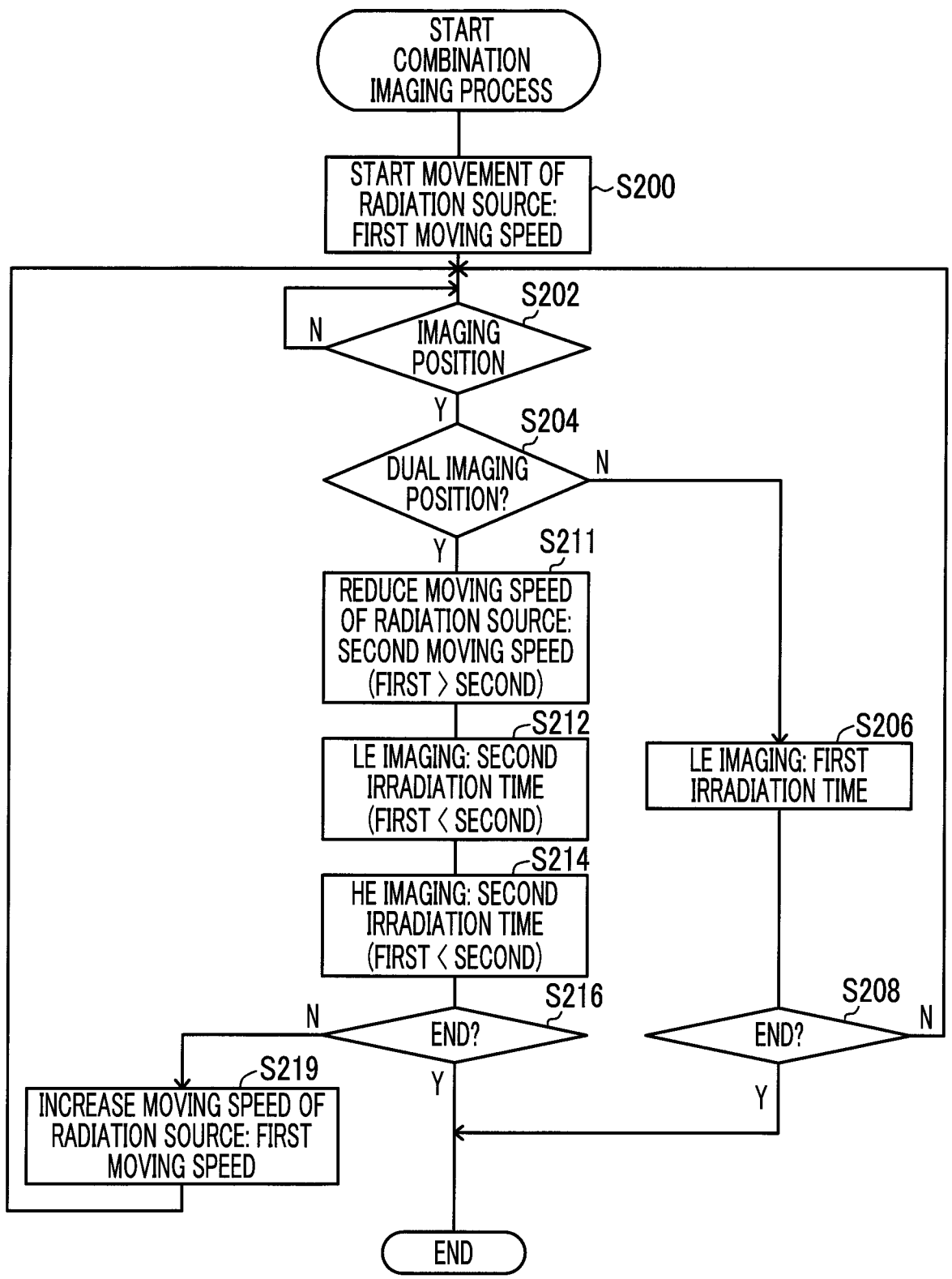
FIG. 14 is a flowchart showing another example of a flow of a combination imaging process in an imaging process according to a second embodiment.

FIG. 14 shows a flowchart showing an example of a flow of the combination imaging process executed by the controller 60 of the mammography apparatus 10 of the embodiment. Since the combination imaging process shown in FIG. 14 is different from the combination imaging process (refer to FIG. 8) of the first embodiment in that a process of step S211 is performed instead of the process of step S210 and a process of step S219 is performed instead of the process of step S218, the different processes will be described.

In step S200, the controller 60 sets the moving speed of the radiation source 29 (radiation irradiation part 28) which is started to be moved by the radiation source driver 68 as a first moving speed. Therefore, in a case where the LE imaging is performed at the imaging position where only the LE imaging is performed (step S206), imaging is performed in a state where the radiation source 29 is moved at the first moving speed.

In step S211, the controller 60 reduces the moving speed of the radiation source 29 from the first moving speed to a second moving speed slower than the first moving speed. In the LE imaging in step S212 and the HE imaging in step S214, imaging is performed in a state where the radiation source 29 is moved at the second moving speed.

Since imaging is performed in a state where the radiation source 29 is moved at the second moving speed as described above, strictly speaking, there is a deviation depending on the second moving speed between the imaging position of the LE imaging in step S212 and the imaging position of the HE imaging in step S214. As the deviation is smaller, the image quality of the differential tomographic image 110 is improved, and the detection accuracy of the ROI is improved. Thus, the second moving speed is not particularly limited, but the second moving speed is preferably slower from the viewpoint of the image quality, and is preferably faster from the viewpoint of reducing the imaging time.

In addition, in step S219, the controller 60 increases the moving speed of the radiation source 29 from the second moving speed to the first moving speed, and then the process returns to step S202. The time required for increasing the moving speed from the second moving speed to the first moving speed is not particularly limited, but is preferable to be at least a time during which the moving speed is increased to the first moving speed before reaching the next imaging position, and as the time required for increasing the moving speed is shorter, it is possible to reduce the time for the entire combination imaging process.

In this manner, even in the mammography apparatus 10 of the embodiment, in the combination imaging, at the imaging position where only the LE imaging is performed, the first radiation image is captured by the radiation detector 11 by emitting the radiation R with low energy in a state where the radiation source 29 is moved. Meanwhile, in the combination imaging, at the imaging position where the dual imaging is performed, in a state where the moving speed of the radiation source 29 is made slower than that at the imaging position where only the LE imaging is performed, the first radiation image is captured by the radiation detector 11 by emitting the radiation R with low energy and the second radiation image is captured by the radiation detector 11 by emitting the radiation R with high energy.

With the mammography apparatus 10 of the embodiment, at the imaging position where only the LE imaging is performed, the moving speed of the radiation source 29 is not reduced, and thus it is possible to further reduce the time required until the capturing of the first radiation image and the second radiation image is completed. Accordingly, since the time required for the combination imaging process is reduced, the time required for the imaging process (refer to FIG. 5) is reduced.

Accordingly, even in the mammography apparatus 10 of the embodiment, since it is possible to reduce the time required for the imaging process in step S16 shown in FIG. 4, it is possible to reduce the duration time for pressing the mamma W. In this manner, with the mammography apparatus 10 of the embodiment, it is possible to reduce a burden on the test subject.

Third Embodiment

In the mammography apparatus 10 of each embodiment described above, the dose of the radiation R emitted in the imaging is the same regardless of the type of imaging, but the dose of the radiation R to be emitted may be differentiated depending on the type of imaging or the like. In the embodiment, the mammography apparatus 10 in which the dose of the radiation R emitted in the LE imaging and the dose of the radiation R emitted in the HE imaging are different will be described.

Since the configuration of the mammography apparatus 10 is the same as in the first embodiment, description thereof will not be repeated. In the embodiment, since a partial process of the combination imaging process of the imaging process executed by the controller 60 of the mammography apparatus 10 is different from the combination imaging process (refer to FIG. 8) of the first embodiment, the different process will be described.

Figure 15:
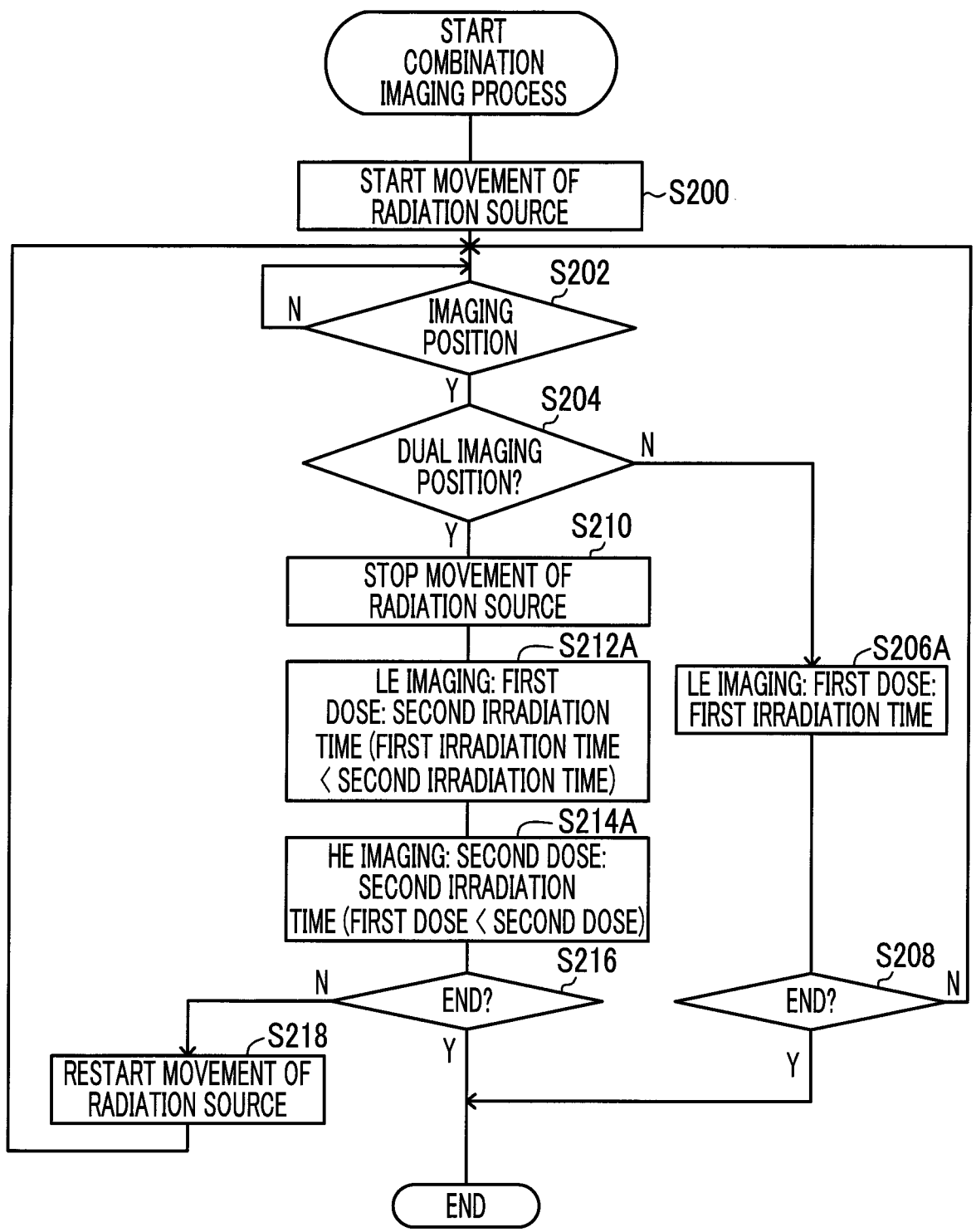
FIG. 15 is a flowchart showing an example of a flow of a combination imaging process in an imaging process according to a third embodiment.

FIG. 15 shows a flowchart showing an example of a flow of the combination imaging process executed by the controller 60 of the mammography apparatus 10 of the embodiment. The combination imaging process shown in FIG. 15 is performed in the same manner as the combination imaging process (refer to FIG. 8) of the first embodiment described above except for the LE imaging in step S206A, the LE imaging in step S212A, and the HE imaging in step S214A.

As shown in FIG. 15, in step S206A in case of the imaging position where only the LE imaging is performed (hereinafter, simply referred to as "case of only the LE imaging"), the controller 60 performs the LE imaging by emitting the radiation R with a first dose for a first irradiation time. In addition, in step S212A in case of performing the dual imaging, the controller 60 performs the LE imaging by emitting the radiation R with the first dose for a second irradiation time. Further, in step S214A, by increasing the tube current to be applied to the radiation source 29, the controller 60 performs the HE imaging by emitting the radiation R with a second dose, which is greater than the first dose, for the second irradiation time. In the embodiment, the second dose is the same as the dose of the radiation R emitted in the imaging in the above-described embodiments. Therefore, the first dose is smaller than the dose of the radiation R emitted in the imaging in the above-described embodiments. As described above, in the embodiment, the increase or decrease of the dose is adjusted by the tube current, and the dose is increased as the tube current is increased.

In general, in the capturing of the radiation image, as the dose of the emitted radiation R is smaller, the signal/noise ratio (SN ratio) of the obtained radiation image is decreased, and thus the image quality deteriorates.

In addition, in general, in case of generating the differential image from the first radiation image and the second radiation image obtained in the dual imaging, an influence of the image quality of the first radiation image obtained in the LE imaging on the image quality of the differential image is smaller than an influence of the image quality of the second radiation image obtained in the HE imaging on the image quality of the differential image. Therefore, the image quality of the first radiation image obtained in the LE imaging may not be the same as or smaller than the image quality of the second radiation image obtained in the HE imaging, in some cases.

In the mammography apparatus 10 of the embodiment, the first dose of the radiation R emitted in the LE imaging is smaller than the second dose of the radiation R emitted in the HE imaging. What value to be set for the first dose and how much less the first dose than the second dose may be determined in advance according to the user's desired image quality of the differential tomographic image or the 'image quality of the tomographic image generated from the first radiation image.

In the mammography apparatus 10 of the embodiment, the first dose of the radiation R in the LE imaging is smaller than the second dose of the radiation R in the HE imaging. Accordingly, with the mammography apparatus 10 of the embodiment, it is possible to reduce the total amount (amount of radiation exposure) of the radiation R to be emitted to the mamma W and to reduce deterioration in image quality of the radiation image as compared with a case where the first dose and the second dose are the same.

Fourth Embodiment

In the embodiment, the mammography apparatus 10 in which the dose of the radiation R emitted in the LE imaging of the dual imaging and the dose of the radiation R emitted in the other imaging are different will be described.

Since the configuration of the mammography apparatus 10 is the same as in the first embodiment, description thereof will not be repeated. In the embodiment, since a partial process of the combination imaging process of the imaging process executed by the controller 60 of the mammography apparatus 10 is different from the combination imaging process (refer to FIG. 8) of the first embodiment and the combination imaging process (refer to FIG. 15) of the third embodiment, the different process will be described.

Figure 16:
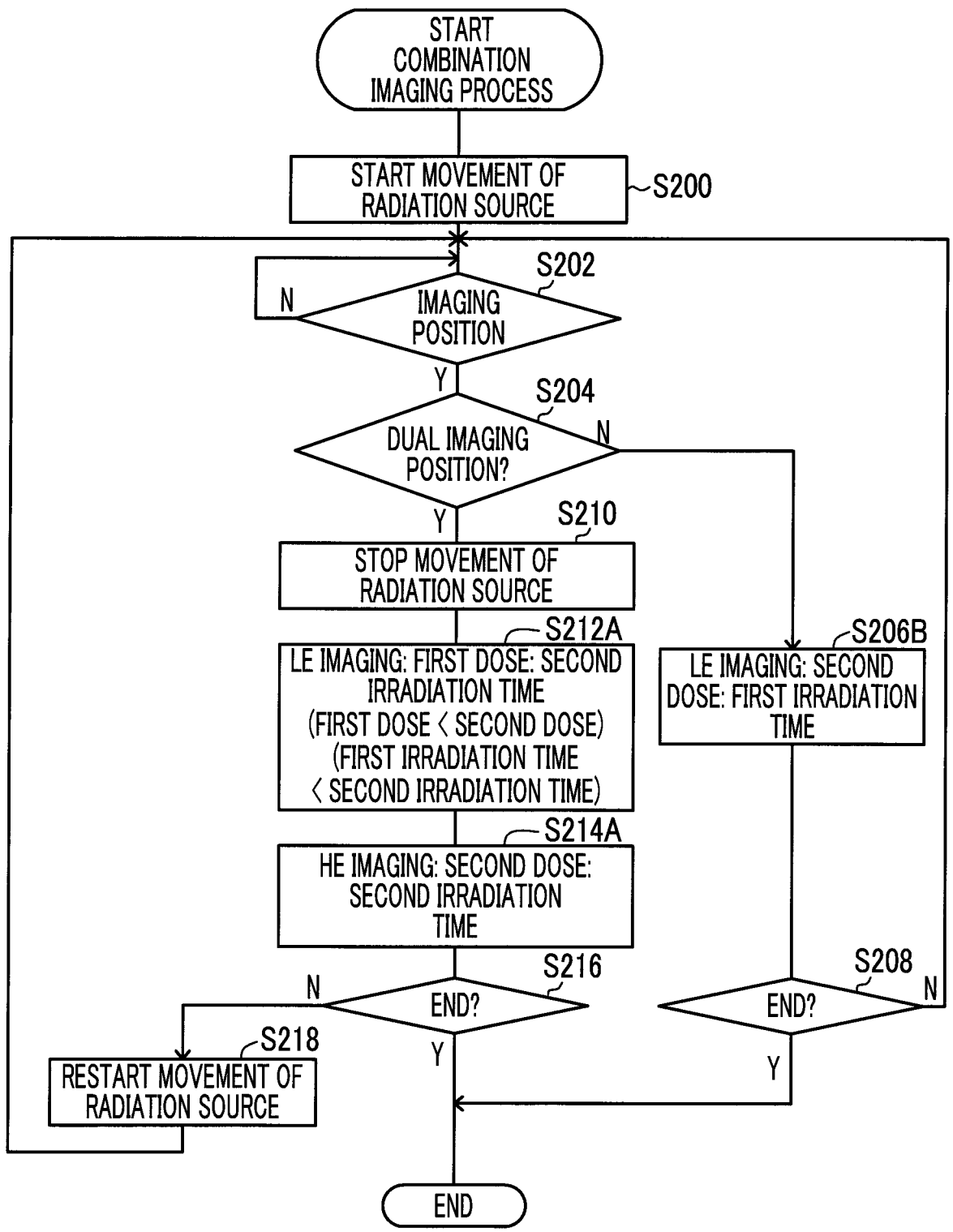
FIG. 16 is a flowchart showing an example of a flow of a combination imaging process in an imaging process according to a fourth embodiment.

FIG. 16 shows a flowchart showing an example of a flow of the combination imaging process executed by the controller 60 of the mammography apparatus 10 of the embodiment. The combination imaging process shown in FIG. 16 is performed in the same manner as the combination imaging process (refer to FIG. 8) of the first embodiment described above except for the LE imaging in step S206B, the LE imaging in step S212A, and the HE imaging in step S214A.

The LE imaging in step S212A and the HE imaging in step S214A are performed in the same manner as in steps S212A and S214A of the combination imaging process (refer to FIG. 15) of the third embodiment. That is, the dual imaging is the same as the dual imaging of the combination imaging process of the third embodiment.

Meanwhile, as shown in FIG. 16, in step S206B in case of only the LE imaging, the controller 60 performs the LE imaging by emitting the radiation R with the second dose for the first irradiation time. In the mammography apparatus 10 of the embodiment, the dose of the radiation R is adjusted by adjusting the tube current.

That is, in the mammography apparatus 10 of the embodiment, the dose (first dose) of the radiation R emitted in case of performing the LE imaging of the dual imaging is smaller than the dose (second dose) of the radiation R emitted in case of performing only the LE imaging.

As described above in the third embodiment, in a case where the differential image or the differential tomographic image is generated by using the dual imaging, the image quality of the first radiation image obtained in the LE imaging may be lower than the image quality of the second radiation image obtained in the HE imaging, in some cases. Therefore, the dose of the radiation R in the LE imaging can be lower than the dose of the radiation R in the HE imaging.

Accordingly, with the mammography apparatus 10 of the embodiment, it is possible to reduce the total amount (amount of radiation exposure) of the radiation R to be emitted to the mamma W as compared with a case where the first dose and the second dose are the same.

With the mammography apparatus 10 of the embodiment, by setting the dose of the radiation R in case of only the LE imaging to the second dose greater than the first dose, it is possible to reduce deterioration in image quality of the tomographic image generated from the first radiation image obtained in the LE imaging.

Fifth Embodiment

In the embodiment, the mammography apparatus 10 in which the dose of the radiation R emitted in case of only the LE imaging and the dose of the radiation R emitted in the dual imaging are different will be described.

Since the configuration of the mammography apparatus 10 is the same as in the first embodiment, description thereof will not be repeated. In the embodiment, since a partial process of the combination imaging process of the imaging process executed by the controller 60 of the mammography apparatus 10 is different from the combination imaging process (refer to FIG. 8) of the first embodiment, the combination imaging process (refer to FIG. 15) of the third embodiment, and the combination imaging process (refer to FIG. 16) of the fourth embodiment, the different process will be described.

Figure 17:
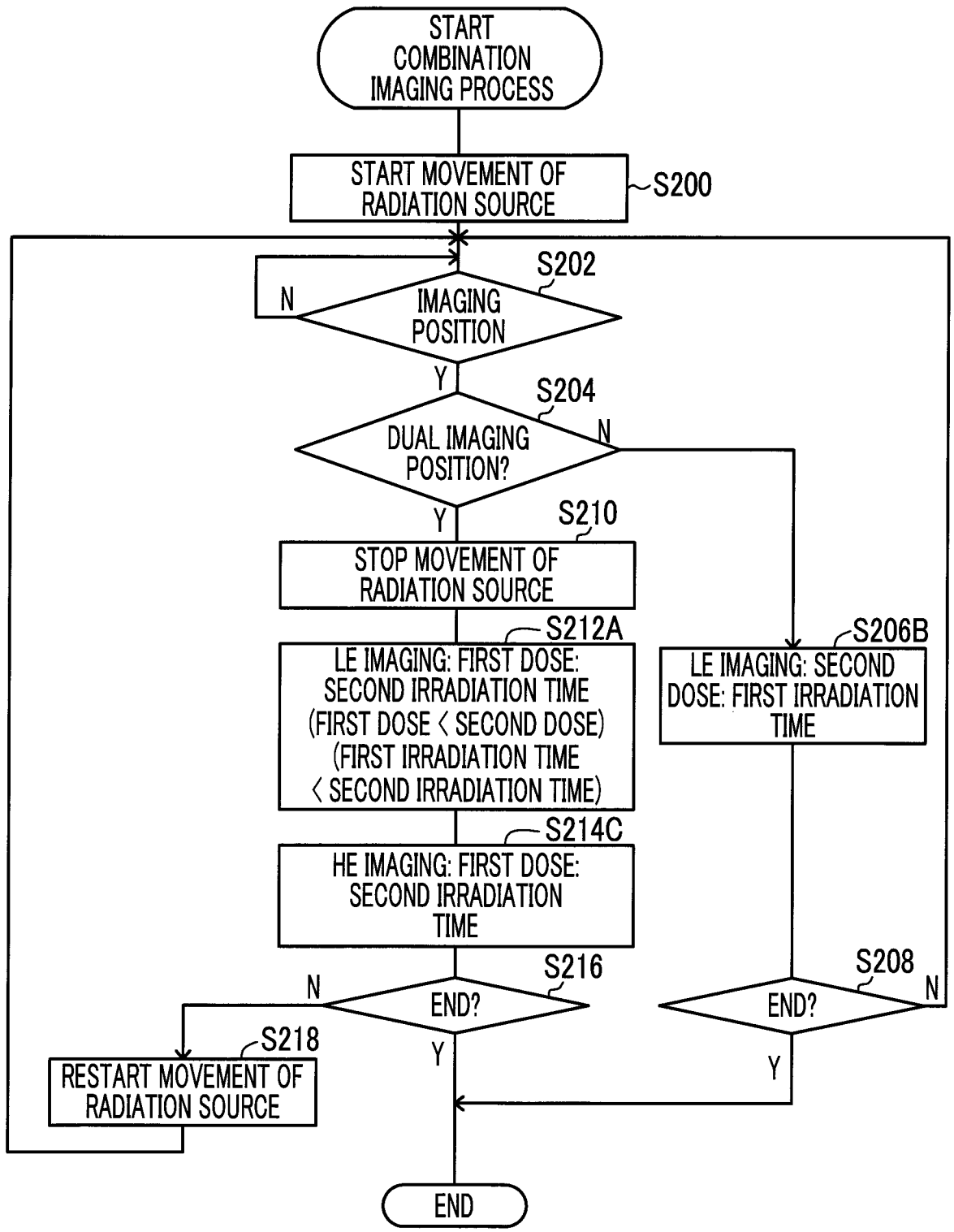
FIG. 17 is a flowchart showing an example of a flow of a combination imaging process in an imaging process according to a fifth embodiment.

FIG. 17 shows a flowchart showing an example of a flow of the combination imaging process executed by the controller 60 of the mammography apparatus 10 of the embodiment. The combination imaging process shown in FIG. 17 is performed in the same manner as the combination imaging process (refer to FIG. 8) of the first embodiment described above except for the LE imaging in step S206B, the LE imaging in step S212A, and the HE imaging in step S214C.

The LE imaging in step S206B is performed in the same manner as in step S206B of the combination imaging process (refer to FIG. 16) of the fourth embodiment. In addition, the LE imaging in step S212A is performed in the same manner as in step S212A of the combination imaging process (refer to FIG. 15) of the third embodiment.

Meanwhile, as shown in FIG. 17, in step S214C in case of performing the dual imaging, the controller 60 performs the HE imaging by emitting the radiation R with the first dose for the second irradiation time. In the mammography apparatus 10 of the embodiment, the dose of the radiation R is adjusted by adjusting the tube current.

That is, in the mammography apparatus 10 of the embodiment, the dose (first dose) of the radiation R emitted in case of performing the dual imaging is smaller than the dose (second dose) of the radiation R emitted in case of performing only the LE imaging.

In the mammography apparatus 10 of the embodiment, the differential image or the differential tomographic image obtained by using the dual imaging is used for observing the contrast-medium image as described in the first embodiment. Therefore, the differential image or the differential tomographic image may be suitable for observing the contrast-medium image, and regarding the image of other parts of the mamma W, it is possible to refer to the tomographic image generated from the first radiation image obtained in the LE imaging. Thus, the quality of the differential image or the differential tomographic image may be lowered than the image quality of the tomographic image, in some cases. Therefore, the dose of the radiation R in the LE imaging and the HE imaging of the dual imaging can be lower than the dose of the radiation R in case of only the LE imaging.

Accordingly, with the mammography apparatus 10 of the embodiment, it is possible to obtain the radiation image of a proper image according to the user's desire and to reduce the total amount (amount of radiation exposure) of the radiation R to be emitted to the mamma W.

As described above, the mammography apparatus 10 of the embodiment comprises the radiation source driver 68 that moves the radiation source 29 to a plurality of imaging positions including a first imaging position where LE imaging of emitting radiation R with low energy from the radiation source 29 to capture a radiation image by the radiation detector 11 is performed, and a second imaging position where the LE imaging and HE imaging of emitting radiation R with high energy different from the low energy from the radiation source 29 to capture a radiation image by the radiation detector 11 are performed, and the controller 60 that causes the radiation detector 11 to perform the LE imaging at the first imaging position in a state where the radiation source 29 is moved by the radiation source driver 68, and causes the radiation detector 11 to perform the LE imaging and the HE imaging at the second imaging position in a state where the movement of the radiation source 29 is stopped or the radiation source 29 is moved at a moving speed slower than that at the first imaging position by the radiation source driver 68.

In this manner, with the mammography apparatus 10 of each embodiment described above, at the imaging position where only the LE imaging is performed, the movement of the radiation source 29 is not stopped or the moving speed of the radiation source 29 is not reduced, and thus it is possible to further reduce the time required until the capturing of the first radiation image and the second radiation image is completed.

Accordingly, with the mammography apparatus 10 of each embodiment described above, since the time required for the combination imaging process is reduced, the time required for the imaging process (refer to FIG. 5) is reduced. In this manner, with the mammography apparatus 10 of each embodiment described above, as described above, it is possible to reduce the duration time for pressing the mamma W and to reduce a burden on the test subject.

Figure 18:
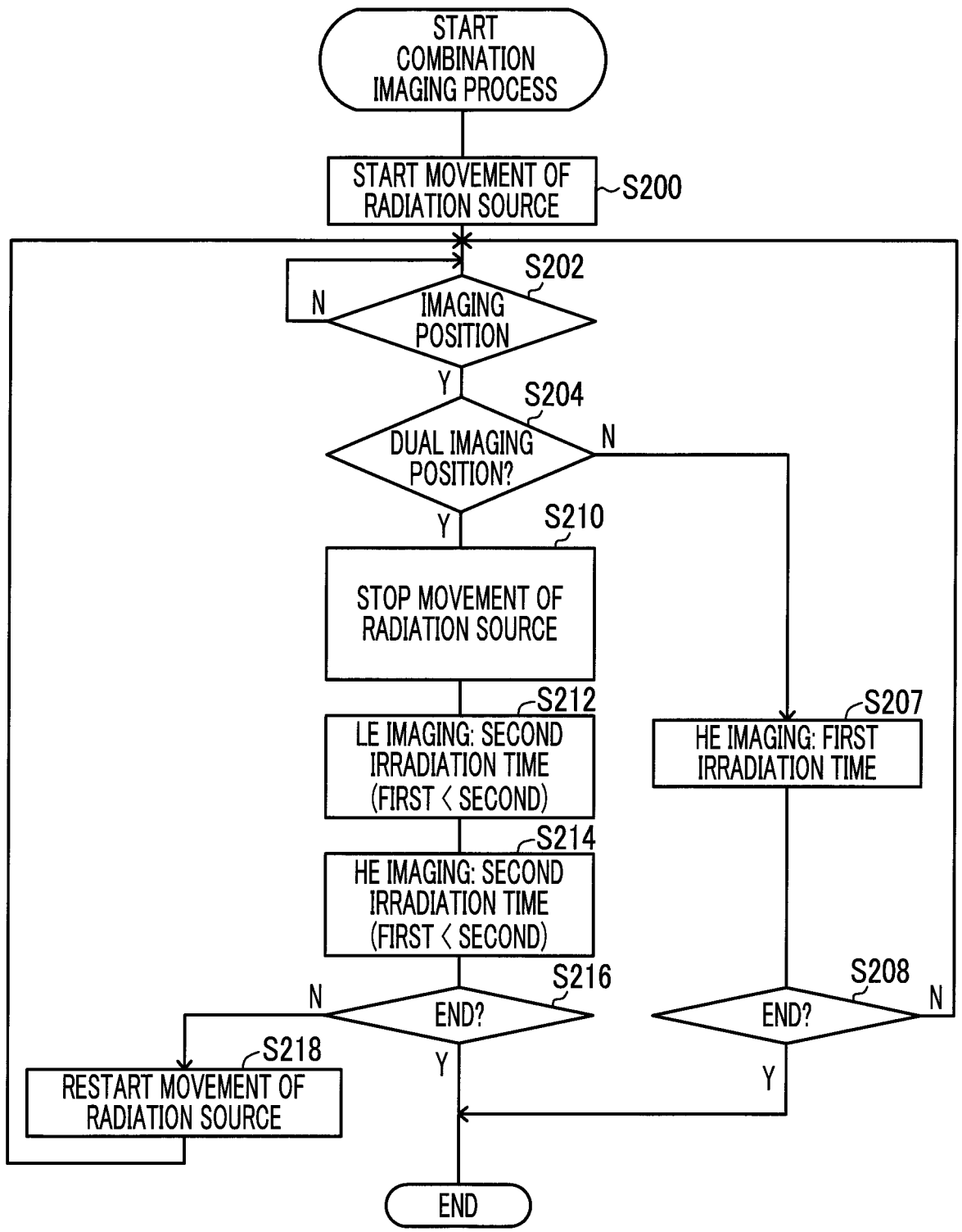
FIG. 18 is a flowchart showing another example of a flow of an imaging process executed by a mammography apparatus according to an embodiment.

In each embodiment described above, an aspect in which the normal tomosynthesis imaging combined with the dual imaging of the combination imaging is the LE imaging has been described, but an aspect in which the normal tomosynthesis imaging combined with the dual imaging of the combination imaging is the HE imaging may be adopted. FIG. 18 shows a flowchart showing an example of a flow of the combination imaging process executed by the mammography apparatus 10 of this case. Since the combination imaging process shown in FIG. 18 is different from the combination imaging process (refer to FIG. 8) of the first embodiment in that a process of step S207 is performed instead of the process of step S206, the different processes will be described.

In step S207, the controller 60 emits radiation R with high energy from the radiation source 29 with the irradiation time as the first irradiation time to perform the HE imaging. In this case, as described above, the HE imaging is performed by emitting radiation R from the radiation source 29 in a state where the radiation irradiation part 28 is moved. In a case where the filter positioned within the irradiation field is not the Cu filter 44 (which is the Rh filter 42), the controller 60 positions the Cu filter 44 within the irradiation field by moving the Rh filter 42 and the Cu filter 44. The second radiation image captured in the HE imaging by the radiation detector 11 is output to the console 6 from the mammography apparatus 10.

In this case, in steps S304 and S332 of the image display process (refer to FIG. 11), the tomographic image can be generated from the second radiation image instead of the first radiation image.

In each embodiment described above, an aspect in which, in the dual imaging, the irradiation time for radiation R in the LE imaging and the irradiation time for radiation R in the HE imaging are the same (second irradiation time) has been described, but an aspect in which the irradiation times for radiation R are different may be adopted. For example, in the dual imaging, by setting the irradiation time for radiation R in the LE imaging to be shorter than the irradiation time for radiation R in the HE imaging, it is possible to reduce the time required for the combination imaging process. In a case where the irradiation time is reduced, the dose of the radiation R to be emitted is reduced, but as described above, it is allowable that the image quality of the first radiation image is not equal to the image quality of the second radiation image. Therefore, it is possible to set the irradiation time for the radiation R in the LE imaging to be shorter than the irradiation time of the radiation R in the HE imaging.

In case of performing the dual imaging, an aspect in which at each imaging position, the movement of the radiation source 29 is stopped in the first embodiment and the moving speed of the radiation source 29 is made slow in the second embodiment has been described, but an aspect in which the movement of the radiation source 29 is stopped at some of the imaging positions and the moving speed of the radiation source 29 is made slow at the other imaging positions may be adopted. For example, the LE imaging and the HE imaging may be performed in a state where the movement of the radiation source 29 is stopped only at the positions where the incidence angle of the radiation R is 0 degrees, which is equivalent to the imaging position in case of capturing the simple image, and performed in a state where the moving speed of the radiation source 29 is made slow at the other imaging positions.

Figure 19:
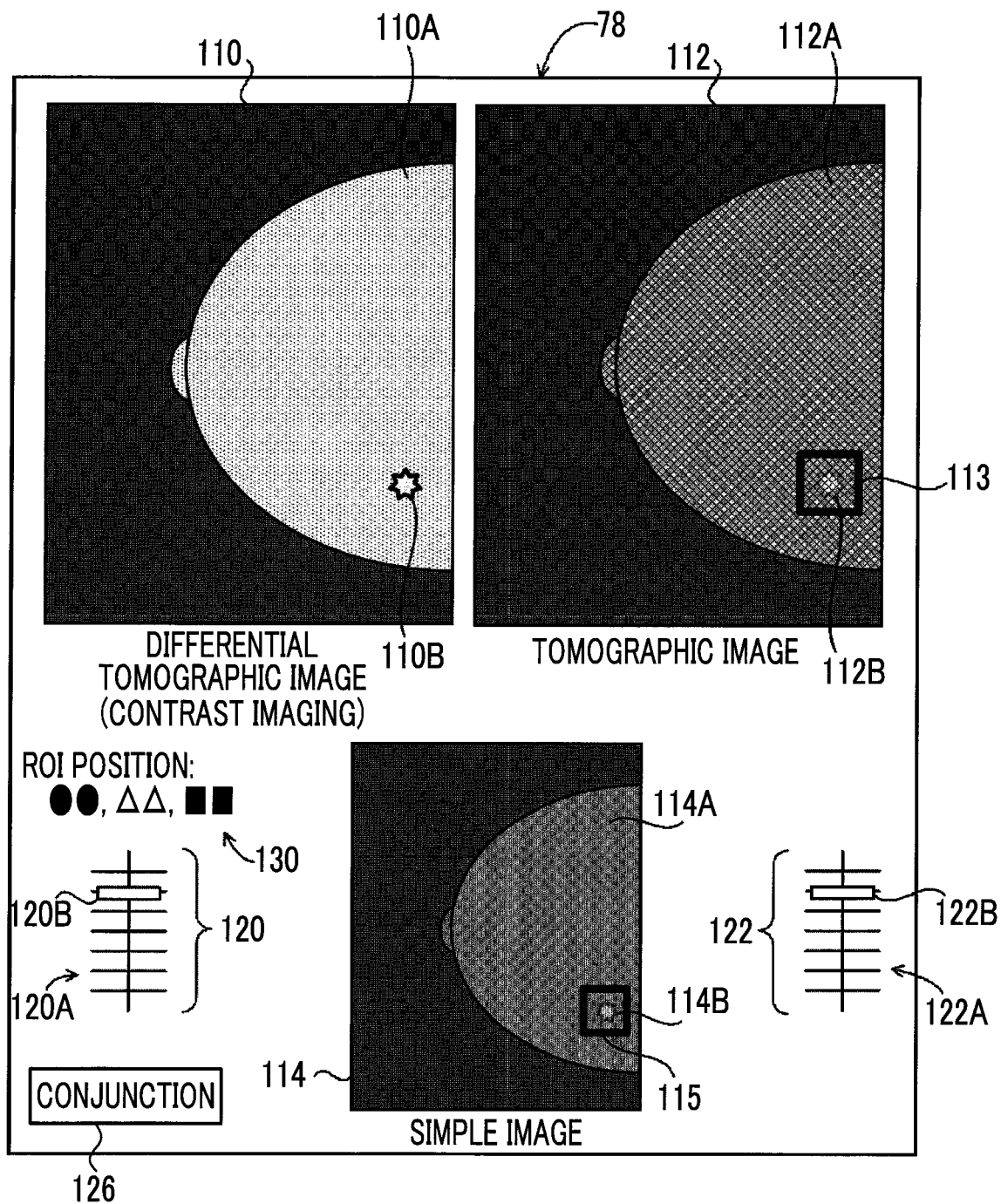
FIG. 19 is a diagram showing an example of a display state of a differential tomographic image, a tomographic image, and a simple image.

The display method of the differential tomographic image 110 and the tomographic image 112 is not limited to the aspect described in the first embodiment. For example, for the same mamma W, the controller 70 of the console 6 may acquire radiation images other than the differential tomographic image 110 and the tomographic image 112 and display the acquired radiation images with the differential tomographic image 110 and the tomographic image 112 on the display 78. As an example, FIG. 19 shows a display example of the differential tomographic image 110, the tomographic image 112, and the simple image 114 on the display 78. In the example shown in FIG. 19, the differential tomographic image 110 and the tomographic image 112 are displayed side by side as in the example shown in FIG. 12, and the simple image 114 is also displayed. In the simple image 114 shown in FIG. 19, a mamma 114A and a contrast medium 114B are shown, and a mark 115 for emphasizing the region of the ROI is further displayed. With the display aspect shown in the example of FIG. 19, the user can easily compare the contrast-medium image in each of a plurality of types of radiation images.

In each embodiment described above, an aspect in which the dual imaging is applied to the contrast imaging has been described, but the dual imaging may be applied to imaging for other purposes without being limited thereto.

In addition, the imaging process and the image display process that are executed by the CPU executing software (program) in each embodiment described above may be executed by various processors other than the CPU. Furthermore, the various processors in this case include a programmable logic device (PLD) of which the circuit configuration can be changed after manufacture, such as a field programmable gate array (FPGA), and a dedicated electrical circuitry, which is a processor having a circuit configuration designed exclusively to execute a specific process, such as an application specific integrated circuit (ASIC). Further, the imaging process and the image display process may be executed by one of the various processors, or executed by the combination of the same or different kinds of two or more processors (for example, combination of a plurality of FPGAs, combination of the CPU and the FPGA, or the like). Furthermore, the hardware structures of the various processors are more specifically electrical circuitry where circuit elements, such as semiconductor elements, are combined.

In each embodiment described above, an aspect in which the various programs stored in the controller 60 of the mammography apparatus 10 and the controller 70 of the console 6 are stored (installed) in the ROMs (60B, 70B) of the controller 60 and the controller 70 in advance has been described, but the embodiment is not limited thereto. The imaging processing program and the image display processing program may be provided by being recorded in a recording medium such as a compact disk read only memory (CD-ROM), a digital versatile disk read only memory (DVD-ROM), and a Universal Serial Bus (USB) memory. In addition, the imaging processing program and the image display processing program may be downloaded from external devices via a network.

The radiation in each embodiment described above is not particularly limited, and X-rays, y-rays, or the like may be used.

The configurations, operations, and the like of the radiation image capturing system 1, the console 6, the mammography apparatus 10, and the like described in each embodiment described above are examples, and may be modified in accordance with situations in a range without departing from the concept of the invention. It is needless to say that the embodiments described above can be combined appropriately.

The disclosure of Japanese Patent Application No. 2017-140326 filed on Jul. 19, 2017 is incorporated herein by reference in its entirety.

All documents, patent applications, and technical standards described in this specification are incorporated herein to the same extent as in a case where each of the documents, patent applications, and technical standards is specifically and individually stated by reference.

EXPLANATION OF REFERENCES

1: radiation image capturing system
6: console
10: mammography apparatus
11: radiation detector, 11A: detection surface
12: imaging part
14: base stand part
16: imaging stand
18: holding part
20: pressing plate
22: support part
24: imaging surface
26: support arm
28: radiation irradiation part
29: radiation source
42: Rh filter
44: Cu filter
60, 70: controller
60A, 70A: CPU
60B, 70B: ROM
60C, 70C: RAM
62, 72: storage unit
64, 74: I/F part
66: operation panel
68: radiation source driver
69, 83: bus
76: display driver
78: display
80: operation input detector
82: operation part
100, $100_1$ to $100_5$: imaging position
110: differential tomographic image, 110A: mamma, 110B: contrast medium
112: tomographic image, 112A: mamma, 112B: contrast medium
113, 115: mark
114: simple image, 114A: mamma, 114B: contrast medium
120, 122, 124: slice position information, 120A, 122A, 124A: bar, 120B, 122B, 124B: slider
126: conjunction button
130: ROI position information
134: switch button
CL: normal line
R: radiation
RC: radiation axis
W: mamma
α, θ: angle

What is claimed is:

1. A mammography apparatus comprising:
a radiation source driver that moves a radiation source to a plurality of imaging positions including a first imaging position where first imaging of emitting radiation with first energy from the radiation source to capture a radiation image by a radiation detector is performed, and a second imaging position where the first imaging and second imaging of emitting radiation with second energy different from the first energy from the radiation source to capture a radiation image by the radiation detector are performed; and
a controller that causes the radiation detector to perform the first imaging at the first imaging position in a state where the radiation source is moved by the radiation source driver, and causes the radiation detector to perform the first imaging and the second imaging at the second imaging position in a state where the movement of the radiation source is stopped or the radiation source is moved at a moving speed slower than a moving speed at the first imaging position by the radiation source driver.

2. The mammography apparatus according to claim 1, wherein the controller performs control such that an irradiation time for which radiation is emitted from the radiation source in the first imaging is shorter than an irradiation time for which radiation is emitted from the radiation source in the second imaging.

3. The mammography apparatus according to claim 1, wherein the first energy is lower than the second energy.

4. The mammography apparatus according to claim 1, wherein the first energy is higher than the second energy.

5. The mammography apparatus according to claim 1, wherein the controller performs control such that a dose of the radiation emitted from the radiation source in the first imaging is smaller than a dose of the radiation emitted from the radiation source in the second imaging in a case where the first energy is lower than the second energy.

6. The mammography apparatus according to claim 1, wherein the controller performs control such that a dose of the radiation emitted from the radiation source in the first imaging at the second imaging position is smaller than a dose of the radiation emitted from the radiation source in the first imaging at the first imaging position in a case where the first energy is lower than the second energy.

7. The mammography apparatus according to claim 1, wherein the controller performs control such that a dose of the radiation emitted from the radiation source in the first imaging at the second imaging position and a dose of the radiation emitted from the radiation source in the second imaging at the second imaging position are smaller than a dose of the radiation emitted from the radiation source in the first imaging at the first imaging position.

8. The mammography apparatus according to claim 1, wherein the first energy and the second energy are determined depending on a k absorption end of a contrast medium used in contrast imaging.

9. A radiation image capturing system comprising:
the mammography apparatus according to claim 1; and
an image generation unit that acquires a plurality of first radiation images captured in the first imaging and a plurality of second radiation images captured in the second imaging from the mammography apparatus, generates a tomographic image reconstructed using the plurality of first radiation images, generates a differential image between the plurality of first radiation images at the second imaging position and the plurality of second radiation images at the second imaging position for each second imaging position, and generates a differential tomographic image reconstructed using each generated differential image.

10. The radiation image capturing system according to claim 9, further comprising:
a deriving unit that derives a position of an interesting object of a subject, from the differential tomographic image.

11. The radiation image capturing system according to claim 9,
wherein the image generation unit derives a region of the tomographic image corresponding to a region of an interesting object of a subject detected in the differential tomographic image, and displays the tomographic image in which the derived region is emphasized on a display.

12. The radiation image capturing system according to claim 9,
wherein the image generation unit displays the tomographic image and the differential tomographic image side by side on a display.

13. The radiation image capturing system according to claim 9,
wherein the image generation unit displays the tomographic image and the differential tomographic image in a superimposed manner on a display.

14. An image processing apparatus comprising:
an acquisition unit that acquires a plurality of first radiation images captured in first imaging and a plurality of second radiation images captured in second imaging from the mammography apparatus according to claim 1; and
an image generation unit that generates a tomographic image reconstructed using the plurality of first radiation images acquired by the acquisition unit, generates a differential image between the plurality of first radiation images captured in the first imaging at the second imaging position and the plurality of second radiation images for each second imaging position, and generates a differential tomographic image reconstructed using the generated differential image.

15. An image processing method comprising:
acquiring a plurality of first radiation images captured in first imaging and a plurality of second radiation images captured in second imaging from the mammography apparatus according to claim 1;

generating a tomographic image reconstructed using the plurality of acquired first radiation images;

generating a differential image between the plurality of first radiation images captured in the first imaging at the second imaging position and the plurality of second radiation images for each second imaging position; and generating a differential tomographic image reconstructed using the generated differential image.

16. A non-transitory computer readable medium storing a program that causes a computer to execute a process, the process comprising:

acquiring a plurality of first radiation images captured in first imaging and a plurality of second radiation images captured in second imaging from the mammography apparatus according to claim 1;

generating a tomographic image reconstructed using the plurality of acquired first radiation images;

generating a differential image between the plurality of first radiation images captured in the first imaging at the second imaging position and the plurality of second radiation images for each second imaging position; and generating a differential tomographic image reconstructed using the generated differential image.

17. A control method of a mammography apparatus comprising a radiation source driver that moves a radiation source to a plurality of imaging positions including a first imaging position where first imaging of emitting radiation with first energy from the radiation source to capture a radiation image by a radiation detector is performed, and a second imaging position where the first imaging and second imaging of emitting radiation with second energy different from the first energy from the radiation source to capture a radiation image by the radiation detector are performed, the control method comprising:

controlling the radiation detector to perform the first imaging at the first imaging position in a state where the radiation source is moved by the radiation source driver; and controlling the radiation detector to perform the first imaging and the second imaging at the second imaging position in a state where the movement of the radiation source is stopped or the radiation source is moved at a moving speed slower than a moving speed at the first imaging position by the radiation source driver.

18. A non-transitory computer readable medium storing a program that causes a computer to execute a process, the process to control a mammography apparatus comprising a radiation source driver that moves a radiation source to a plurality of imaging positions including a first imaging position where first imaging of emitting radiation with first energy from the radiation source to capture a radiation image by a radiation detector is performed, and a second imaging position where the first imaging and second imaging of emitting radiation with second energy different from the first energy from the radiation source to capture a radiation image by the radiation detector are performed, the process comprising:

controlling the radiation detector to perform the first imaging at the first imaging position in a state where the radiation source is moved by the radiation source driver; and controlling the radiation detector to perform the first imaging and the second imaging at the second imaging position in a state where the movement of the radiation source is stopped or the radiation source is moved at a moving speed slower than a moving speed at the first imaging position by the radiation source driver.

\* \* \* \* \*